US010869882B2

(12) United States Patent
LeBrun et al.

(10) Patent No.: US 10,869,882 B2
(45) Date of Patent: Dec. 22, 2020

(54) ANIMAL FEED COMPOSITIONS AND METHODS OF USING THE SAME

(71) Applicant: KEMIN INDUSTRIES, INC., Des Moines, IA (US)

(72) Inventors: Jeffrey Richard LeBrun, Ann Arbor, MI (US); Robert Levine, Ann Arbor, MI (US); Geoffrey Paul Horst, Grosse Pointe Farms, MI (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 16/290,699

(22) Filed: Mar. 1, 2019

(65) Prior Publication Data

US 2019/0262381 A1 Aug. 29, 2019

Related U.S. Application Data

(62) Division of application No. 13/773,971, filed on Feb. 22, 2013, now Pat. No. 10,265,340.

(60) Provisional application No. 61/601,891, filed on Feb. 22, 2012.

(51) Int. Cl.
*A61K 31/716* (2006.01)
*A23K 20/163* (2016.01)
*A23K 50/10* (2016.01)
*A23K 50/60* (2016.01)
*A61K 45/06* (2006.01)

(52) U.S. Cl.
CPC .......... *A61K 31/716* (2013.01); *A23K 20/163* (2016.05); *A23K 50/10* (2016.05); *A23K 50/60* (2016.05); *A61K 45/06* (2013.01)

(58) Field of Classification Search
CPC ...... A61K 31/716; A61K 45/06; A23K 50/60; A23K 50/10; A23K 20/163
USPC ......................................... 514/54; 424/278.1
See application file for complete search history.

(56) References Cited

U.S. PATENT DOCUMENTS

| | | | |
|---|---|---|---|
| 4,960,697 A | 10/1990 | Johal et al. |
| 5,082,936 A | 1/1992 | Jamas et al. |
| 5,084,386 A | 1/1992 | Tuse et al. |
| 5,174,821 A | 12/1992 | Matsuoka et al. |
| 5,244,681 A | 9/1993 | Vinci et al. |
| 5,633,369 A | 5/1997 | Jamas et al. |
| 6,214,337 B1 | 4/2001 | Hayen et al. |
| 6,444,448 B1 | 9/2002 | Wheatcroft et al. |
| 6,939,864 B1 | 9/2005 | Johnson et al. |
| 7,396,548 B2 | 7/2008 | Kyle |
| 7,780,783 B2 | 8/2010 | Fukatsu et al. |
| 7,981,447 B2 | 7/2011 | Cox |
| 2003/0219468 A1 | 11/2003 | Raczek et al. |
| 2004/0082539 A1 | 4/2004 | Kelly |
| 2008/0108114 A1 | 5/2008 | Cox et al. |
| 2010/0009901 A1 | 1/2010 | Rabovsky et al. |
| 2010/0233320 A1 | 9/2010 | Sunvold et al. |
| 2010/0272940 A1 | 10/2010 | Shi et al. |
| 2010/0279979 A1 | 11/2010 | Sorgente et al. |
| 2011/0123677 A1 | 5/2011 | Rivera et al. |
| 2011/0293783 A1 | 12/2011 | Wittke |
| 2012/0329752 A1 | 12/2012 | Suzuki |

FOREIGN PATENT DOCUMENTS

| | | |
|---|---|---|
| CA | 2359706 A1 | 8/2000 |
| DE | 19734389 A1 | 2/1999 |
| JP | 2001275654 A * | 10/2001 |
| JP | 2004008063 A | 1/2004 |
| JP | 2011184371 A | 9/2011 |
| WO | 9614873 A2 | 5/1996 |
| WO | 2004105775 A1 | 12/2004 |
| WO | 2009068996 A2 | 6/2009 |
| WO | 2011111707 A1 | 9/2011 |
| WO | 2013126669 A1 | 8/2013 |

OTHER PUBLICATIONS

Takigawa; JP 2001275654 A; Oct. 9, 2001 (Machine-English Translation).*
Chen et al., "Maintenance of the activation of peritoneal macrophages in patients with ovarian cancer by sizofiran and recombinant interferon-gamma," Journal of Biotherapy, vol. 5, No. 5, 1992, pp. 137-143.
Ciucanu et al., "A Simple and Rapid Method for the Permethylation of Carbohydrates," Journal of Carbohydrate Research, vol. 131, 1984, pp. 209-217.
Das et al., "The effect of Euglena viridis on immune response of rohu, Labeo rohita (Ham.)," Journal of Fish and Shellfish Immunology, vol. 26, 2009, pp. 871-876.
Eicher et al., "Supplemental vitamin C and yeast cell wall b-glucan as growth enhancers in newborn pigs and as immunomodulators after an endotoxin challenge after weaning," Journal of Animal Science, vol. 84, 2006, pp. 2352-2360.
European Patent Office, "European Search Report," issued in connection with European Application No. 13751435.2, dated Oct. 5, 2015, 8 pages.
Hayashi et al., "Supplemental Effects of Euglena gracilis in a Casein Diet for Penaeus japonicus," Asian Fisheries Science, vol. 8, 1995, pp. 201-209.
International Searching Authority, "Search Report and Written Opinion," mailed in connection with International Application No. PCT/US2013/027282, dated May 3, 2013, 13 pages.

(Continued)

*Primary Examiner* — Shaojia A Jiang
*Assistant Examiner* — Michael C Henry
(74) *Attorney, Agent, or Firm* — Nyemaster Goode P.C.

(57) ABSTRACT

Immune function of an animal can be modulated by administration of a composition that includes beta glucan. The beta glucan can be derived from *Euglena*, which provides a form of beta glucan that is different from other organisms, where the beta glucan is predominantly unbranched beta-(1,3)-glucan. Beta glucan can also be complexed with a metal, such as zinc, and/or can combined with an animal feed component to form an animal feed composition. Use of such compositions can improve the well being of an animal, and may augment or even replace the use of antibiotics in certain circumstances.

16 Claims, 8 Drawing Sheets

(56) References Cited

OTHER PUBLICATIONS

International Searching Authority, "International Preliminary Report on Patentability," mailed in connection with International Application No. PCT/US2013/027282, dated Aug. 26, 2014, 12 page.

Kuda et al., "Effects of two storage B-1,3-Glucans, laminaran from Eicenia bicyclis and paramylon from Eugelna gracili, on cecal environment and plasma lipid levels in rats," Journal of Functional Foods, vol. 1, 2009, pp. 399-494.

Sonck et al., "The effect of B-Glucans on porcine leukocytes," Journal of Veterinary Immunology of Immunopathology, vol. 135, 2010, pp. 199-207.

Sugiyama et al., "Oral Administration of Paramylon, a B-1,3-D-Glucan Isolated from Euglena gracilis Z Inhibits Development of Atopic Dermatitis-Like Skin Lesions in NC/Nga Mice," Journal of Laboratory Animal Science, Feb. 16, 2010, 9 pages.

Vismara et al., "Stress resistance induced by paramylon treatment in *Artemia* sp.," Journal of Applied Phycology, vol. 16, 2004, pp. 61-67.

York et al., "Isolantion of Characterization of Plant Cell Walls and Cell Wall Components," Journal of Methods in Enzymology, vol. 118, 1985, 38 pages.

Zhang et al., "The Modulating Effect of B-1,3/1,6-glucan Supplementation in the Diet on Performance and Immunological Responses of Broiler Chickens," Asian-Australian Journal of Animal Science, vol. 21, No. 2, Feb. 2008, pp. 237-244.

\* cited by examiner

FIG. 1A
METAL POLYSACCHARIDE COMPLEX:
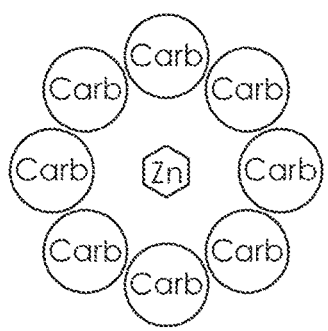
FIG. 1B
METAL PROTEINATE:
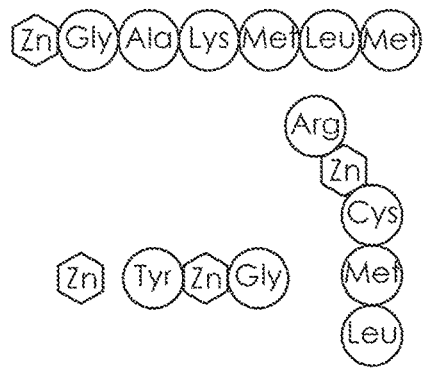
FIG. 1C
METAL AMINO ACID COMPLEX:
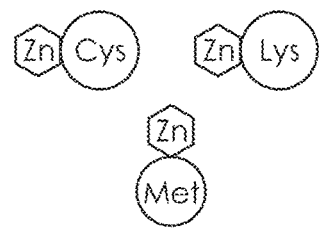
FIG. 1D
METAL PROPIONATE:
FIG. 1E
METAL AMINO ACID CHELATE:
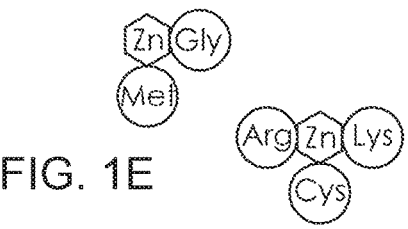
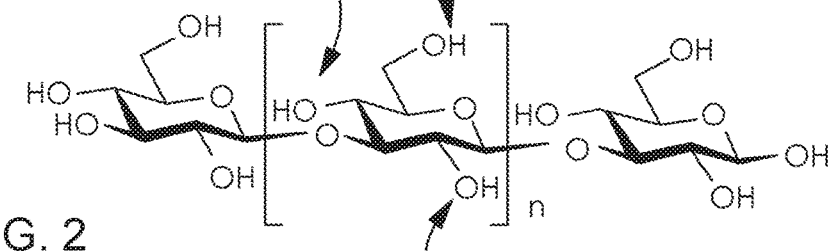
FIG. 2
GLYCOPROTEIN
MANNOPROTEIN
$\beta$-GLUCAN
CHITIN
MANNOPROTEIN
PLASMA MEMBRANE
FIG. 3
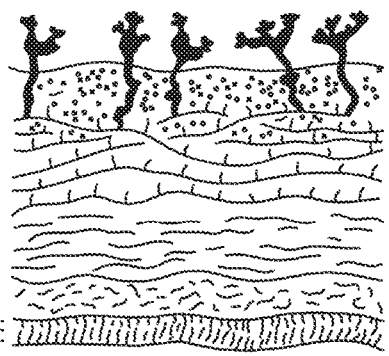

LINEAR BETA-(1,3;1,4)- GLUCAN (OATS, BARLEY)

SIDE-CHAIN-BRANCHED BETA-(1,3;1,6)- GLUCAN (LAMINARIA)

ANIMAL FEED COMPOSITIONS AND METHODS OF USING THE SAME

CROSS-REFERENCE TO RELATED APPLICATIONS

This application is a divisional of U.S. patent application Ser. No. 13/773,971, filed Feb. 22, 2013, entitled ANIMAL FEED COMPOSITIONS AND METHODS OF USING THE SAME, which claims the benefit of U.S. Provisional Application No. 61/601,891, filed on Feb. 22, 2012. The entire disclosures of which are hereby incorporated by reference in their entireties.

FIELD

The present technology relates to beta glucan, trace metals, and complexes of beta glucan and trace metals, and uses thereof to modulate immune function, including providing such compositions as oral supplements or admixed with animal feed.

INTRODUCTION

This section provides background information related to the present disclosure which is not necessarily prior art.

Animals are exposed to many stresses during their lives that have been shown to affect health, growth, mortality, immune system health, and overall well-being of the animal. Currently, antibiotics and other treatments are used to improve the ability of an animal to resist disease and as treatment for a disease. An over-dependence upon antibiotics in modern agriculture and human health has led to widespread antibiotic resistance and led to a desire for more natural ways to promote healthy immune function.

Natural alternatives to antibiotics could be used to combat infectious diseases. Currently, infectious diseases are a leading cause of mortality in the world. In the United States, only cancer and heart disease lead to more deaths in humans than infectious diseases. Antibiotics are often necessary to treat infectious diseases in humans and animals. However, when antibiotics are used continuously, resistant bacterial strains can evolve. Such antibiotic resistance is a serious human health problem and has contributed to increased deaths from antibiotic-resistant bacterial strains like methicillin-resistant *Staphylococcus aureus* (MRSA). For example, antibiotic-resistant strains of bacteria are now cited as the cause of more deaths in the United States than HIV/AIDS.

Despite the need to preserve the integrity of antibiotics for human applications, usage of antibiotics in animal applications comprises over 80% of the total antibiotic use in the United States. From 1985 to 2003, sub-therapeutic usage of antibiotics in animal feed applications has grown tenfold. Development of a non-antibiotic animal feed ingredient that promotes immune system health could help reduce the prevalence of antibiotic-resistant bacterial strains that are also harmful to human beings. Such an ingredient may be more beneficial when used in livestock growth conditions that are antibiotic free. Several nations other than the U.S. do not permit the sub-therapeutic use of antibiotics in animal feed, and may even prohibit the imp0liation of meat products grown using antibiotics from the U.S. In order to be commercially effective, such an ingredient must be cost effective, reliable, safe, and able to be included into the existing water or feed infrastructure.

An example of a compound used to stimulate immune system activity is beta glucan. Beta glucans are polysaccharides connected by beta glycosidic linkages that can be found in various organisms, such as yeast, mushrooms, fungi, cereal grains, and others. Beta-glucan is used as a dietary supplement and various beneficial effects thereof are the subject of various clinical trials. Beta glucan products are currently derived primarily from yeast, where they are extracted from the yeast cell wall using various processes. Examples of these products and processes are described in U.S. Pat. Nos. 5,082,936; 5,633,369; 6,444,448; 7,981,447; and U.S. Pub. Nos. 2008/0108114; and 2004/0082539. Other beta glucan products exist, including ones derived from mushrooms, oats, barley, and kelp. Although these products demonstrate beneficial effects in some cases, these beta glucan products are generally considered to be too expensive for a majority of animal feed applications. The most effective beta glucans produced using these means, for example, were commercially valued between about 50 to 100 USD per kg of beta glucan in 2011, a price that is prohibitive to the majority of people and animal producers.

One reason for the high cost is that the beta glucans in these products are derived from the cell wall of the organism. As such, the resulting beta glucan content of the total biomass used to produce the beta glucan is generally less than ten to fifteen percent. Moreover, the beta glucans contained in an organism's cell wall generally must undergo expensive, multi-stage extraction processes in order to separate the beta glucan from other cellular materials.

Beta glucan structure is also complex. Variations in branching structure, molecular weight, source organism, and method of production and extraction can all affect the efficacy and suitability of different beta glucan products. For example, yeast-derived beta-1,3;1,6-glucans comprise the majority of commercial beta glucan products that are intended to stimulate immune system activity. Beta-1,3:1,4-glucans from oats have been demonstrated as useful for reducing cholesterol, and only these types of beta glucans may be labeled as such according to FDA regulations. Many organisms produce different beta glucan structures, and all beta glucans are not equally effective. Although there is research on the usefulness or efficacy of beta glucans derived from yeast (e.g., U.S. Pat. No 6,939,864), mushrooms, or oats (e.g., U.S. Pub. No. 2011/0123677), there is less research on beta glucans derived from algae or protist-derived sources. Moreover, algae and protists are not produced in commercial quantities that are beneficial for their beta glucan content.

Beta glucans produced by different organisms and extracted with different techniques may have very different effects when fed to animals as a component of an animal feed composition, and this may also affect dosing of the beta glucan. In the document, "Effects of beta-glucan extracted from *Saccharomyces cerevisiae* on growth performance, and immunological and somatotropic responses of pigs challenged with *Escherichia coli* lipopolysaccharide," published in the Journal of Animal Science, Li et al. wrote, "[t]he results of current study indicate that the addition of β-glucan to weaned pig diets is able to offer some benefits on growth performance and immune response to a lipopolysaccharide challenge. However, β-glucans produced by different production methods may have different effects on growth performance and immune function in weaned piglets. Source of β-glucan produced by different methods may vary in their structure, chemical composition, or both, which may influence its activity and the amount that should be added to get a growth response. Therefore, further investigation is warranted to better discern the performance and immune response of β-glucan produced by different methods when it is supplemented to swine diets."

Although beta glucans produced by an algae or a protist such as *Euglena gracilis* may be similar to beta glucans from other sources, these beta glucans are also unique in several ways. For example, the dissimilar evolutionary history that algae and protists have when compared to fungi, plants, or bacteria leads them to produce hundreds of unique compounds, some of which may act as yet-to-determine co-factors to beta glucan. The use of algae or protist-derived beta glucans as a nutritional food and feed supplement may provide lower-cost and potentially higher purity immune modulating supplements for human and animal food supplement applications. In addition, inclusion of beta glucans in the form of an algae or protist meal or supplement would remove the need for potentially harmful or expensive solvent-based extraction-processes, such as the processes that are used to extract beta glucans from the cell walls of yeast or mushrooms, and may permit the inclusion of additional co-factors and nutrients which are supplied by the algae or protist, such as Vitamin E, zinc, Omega 3 fatty acids, and other known or unknown nutritionally beneficial molecules.

In addition to the beneficial immunological aspects relating to beta-glucan, the presence in animal freed of certain trace metals in sufficient quantities, and in biologically available forms, is important for maintaining the well-being of animals. Because essential trace metals are often deficient in commodity feed ingredients, supplemental amounts of these nutrients are often added to feed.

Trace metals have also been shown to effect general immune system performance. Inorganic salts such as zinc oxide and zinc sulfate are often provided as a trace mineral supplement. However, there can be incomplete absorption of these inorganic sources. The p01iion of the trace metal that is not absorbed is likely to pass through an animal's digestive tract into the feces, where it may accumulate. For example, animal waste that is laden with very high concentrations of zinc may be considered to be toxic, with trace metal accumulation causing environmental damage if the animal waste is spread excessively on fields as a fertilizer source, as is a common practice.

Many commercial products exist in which the bioavailability of trace elements is increased compared to an inorganic source of the same metal. The increased bioavailability can be due the association of an organic molecule, which can be a protein, amino acid, or polysaccharide, where the organic molecule is generally termed a ligand. There are different explanations for why organically bound trace metals have increased bioavailability. One explanation is that binding to an organic molecule provides greater stability in the gut, reducing the probability that a stronger agonist that would prevent absorption into the body binds the trace metal. Another explanation is that the organic metal complex is absorbed together through the lining of the intestine. Table 1 summarizes some examples of classifications of trace metal and ligand products.

TABLE 1

Examples of Organic Metal Complexes.

| Description | Examples (U.S. Pat. Nos. unless otherwise noted) |
| --- | --- |
| metal proteinate | 3,440,054; 3,463,858; 3,775,132; 3,969,540; 4,020,158; 4,076,803; 4,103,003; 4,172,072; 5,698,724 |
| metal amino acid | 3,941,818; 3,950,372; 4,067,994; 4,863,898; 4,900,561; 4,948,594; |

TABLE 1-continued

Examples of Organic Metal Complexes.

| Description | Examples (U.S. Pat. Nos. unless otherwise noted) |
| --- | --- |
| complex or chelate | 4,956,188; 5,061,815; 5,278,329; 5,583,243; 6,166,071; 3,950,372; 4,021,569; 4,039,681; 4,067,994; 5,278,329; 4,900,561; 4,948,594; 4,956,188; 5,583,243; 7,129,375 |
| metal propionate | 5,591,878; 5,707,679; 5,795,615; 5,846,581 |
| metal polysaccharide complex | 8,273,393; 4,661,358; EP 0712581 |

FIG. 1 provides visual representations of these various organic metal complexes. Different types of products containing trace elements associated with an organic ligand can further be classified into different groups based on the ligand used in producing the product.

It is desirable to find ways to improve the effectiveness of an animal's immune system against infectious diseases without relying on antibiotics.

SUMMARY

The present technology includes systems, processes, articles of manufacture, and compositions that relate to modulating immune system function by administering a beta glucan to an animal. For example, the beta glucan can be derived from *Euglena*, can be complexed with a trace metal, and/or can be part of animal feed. The well being of an animal can be improved through the administration of beta glucan, where "well being" includes enhancement in one or more of the following aspects: weight gain, conversion efficiency of food to live weight, behavior, disease resistance, stress tolerance, reduced mortality rates, and improved immune function. The source of beta glucan can be a non-toxic, non-pathogenic algae or protist of the genus *Euglena*.

In certain aspects, a method of modulating the immune function of an animal is provided where the method includes administering to the animal a composition comprising beta glucan, the beta glucan comprising linear, unbranched, beta-(1,3)-glucan. The beta glucan can be derived from *Euglena* and can be derived from heterotrophically grown *Euglena*. The beta glucan can also consist essentially of unbranched beta-(1,3)-glucan and can have an average molecular weight of about 200-500 kDa. The beta glucan can also have greater than about 90% unbranched beta-(1,3)-glucan. The beta glucan can be in the native form of paramylon, which is a water insoluble granule, or can be water soluble. The composition can include algae meal, where the algae meal includes the beta glucan. The composition can further include a metal, such as iron, magnesium, lithium, zinc, copper, chromium, nickel, cobalt, vanadium, molybdenum, manganese, selenium, iodine, and combinations thereof. The beta glucan and the metal can form a complex and in a celtain embodiment comprises a zinc beta glucan complex. Administering the composition can include adding the composition to the animal's diet or drinking water. The composition can also include an animal feed component.

In various aspects, an animal feed composition is provided that includes a linear, unbranched beta-(1,3)-glucan and an animal feed component.

In some aspects, a composition is provided that includes a complex of a metal and a beta glucan.

The present technology demonstrates that beta glucans can be produced at a low cost by using an algae or protist such as *Euglena* sp. using controlled growth methods. The structure of these beta glucans is different from the beta glucans produced using other organisms. One major difference is that while other organisms produce beta glucans incorporated into their cell wall, the genus of protists known as *Euglena* can produce beta glucan, including a particulate form of beta glucan, known as paramylon, that is not incorporated into the structure of the cell wall. Rather, *Euglena* accumulates beta glucan as a water-insoluble granule in the cytoplasm and utilizes this form of beta glucan as a form of carbohydrate energy storage, Under optimized growth conditions, it is possible to achieve concentrations of beta glucan where the net beta glucan weight is greater than 20% to 80% of the total dry weight proportion of the biomass. Achieving these levels of production efficiency can be complicated by the fact that growth of the *Euglena* is achieved in selective conditions that compensate for the faster growth rates of yeast, fungi, and other microorganisms that may be competing for the same carbon source as the *Euglena*. The present technology provides means to maximize *Euglena* growth while minimizing competing microorganism growth. The beta glucan compounds produced by *Euglena* are not the same as other products that are produced using yeast and other organisms, but the beta glucans from *Euglena* are effective at improving immune function. A further benefit is that beta glucan production cost can be less than ½ to ⅕ the production cost of beta glucans that are produced using yeast.

In other embodiments, the present technology includes a composition comprising an effective amount of beta glucan produced by an algae or protist such as *Euglena*, where the composition is used to improve the well-being of an animal. Lower-cost beta glucan feed additives produced using algae therefore provide affordable and natural alternatives to antibiotics and other immune-improving substances for use in animals that can benefit animal husbandry, aquaculture, and even human health applications.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A depicts a representation of an organic metal complex for a metal polysaccharide complex.

FIG. 1B depicts a representation of an organic metal complex for a metal proteinate complex.

FIG. 1C depicts a representation of organic metalcomplex for a metal amino acid complex.

FIG. 1D depicts a representation of an organic metal complex for a metal propionate complex.

FIG. 1E depicts a representation of an organic metal complex for a metal amino acid chelate.

FIG. 2 depicts a beta-1,3 glucan chain with other branching locations indicated. Paramylon, a form of beta glucan from *Euglena*, is unique in that it consists almost entirely of linear, beta-1,3-branches.

FIG. 3 illustrates a yeast cell wall containing beta glucan that is embedded into the cell wall. Unlike in *Euglena gracilis*, extraction and separation processes are necessary to make the beta-1,3;1,6-glucan from yeast fully bioavailable to immune cell receptors.

Figure 4A:
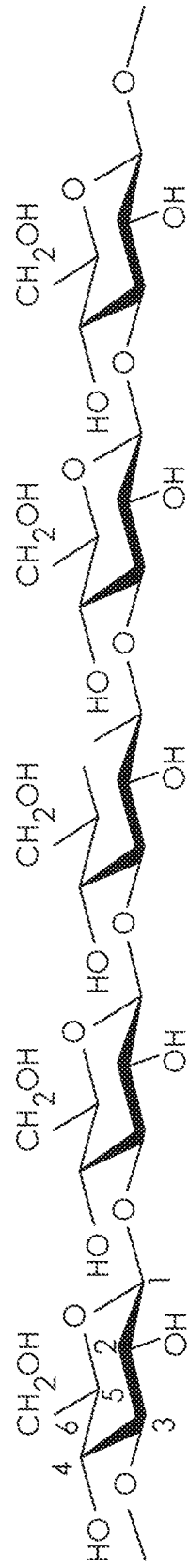

FIGS. 4A-D illustrate the linkage differences between beta glucan branching structures based on the source of the beta glucan, where FIG. 4A illustrates *Euglena* produce beta-1,3 glucans called "Paramylon."

Figure 4B:
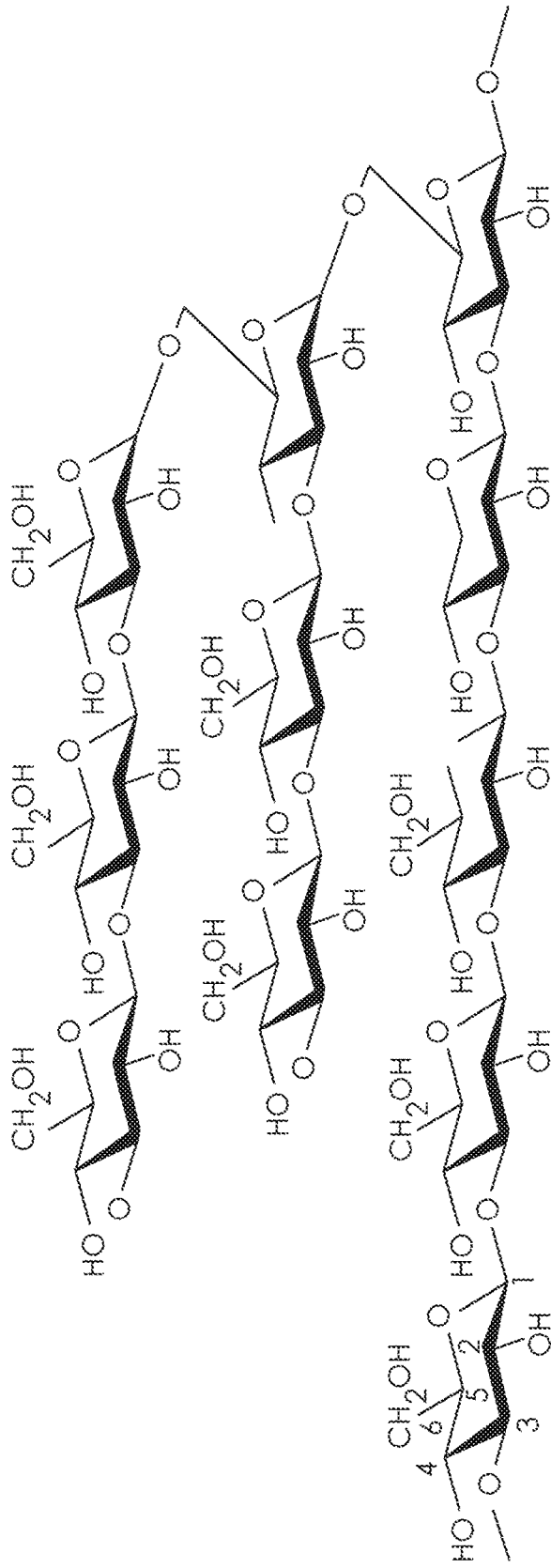

FIG. 4B illustrates yeast-derived products consist of beta-1,3;1,6-branches that are extracted from the cell walls of yeast.

Figure 4C:
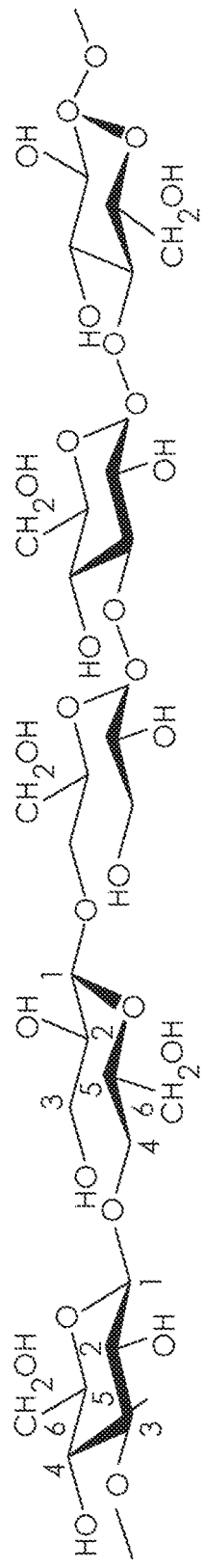

FIG. 4C illustrates beta-1,3;1,4-glucans are more commonly derived from oats or barely and have been demonstrated to reduce cholesterol.

Figure 4D:
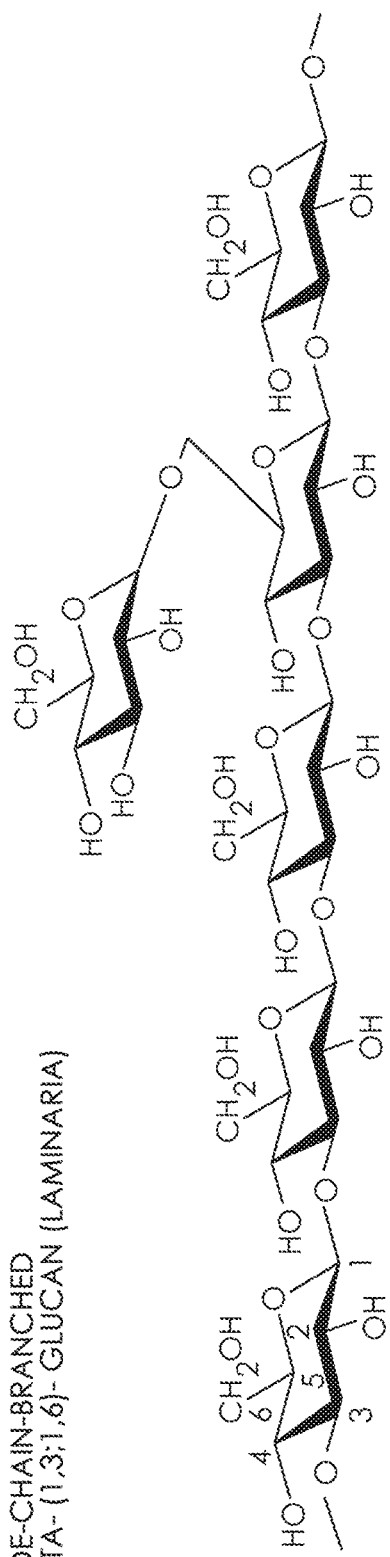

FIG. 4D illustrates Laminaria produce side-chain branched beta-1,3;6-glucans.

Figure 5:
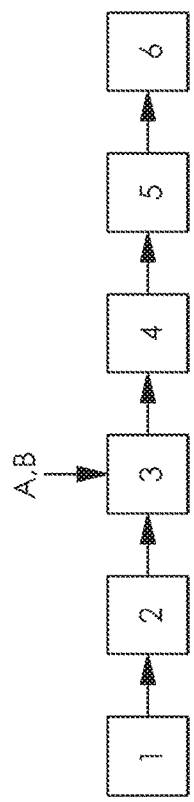

FIG. 5 is a schematic of an embodiment of a fermentation process according to the present technology.

Figure 6:
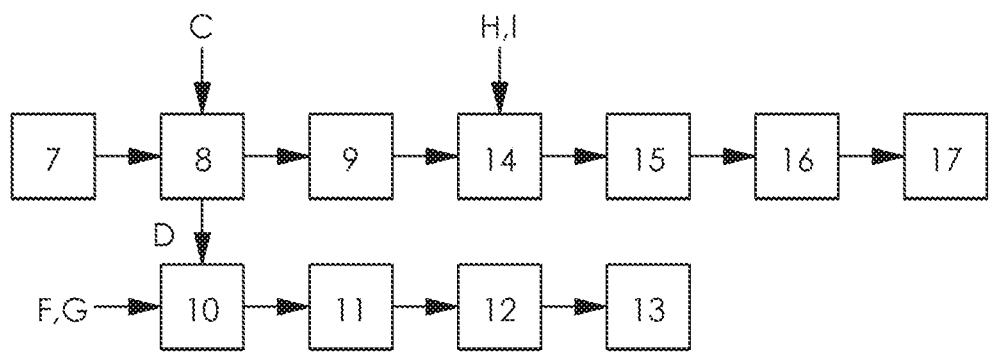

FIG. 6 is a schematic of another embodiment of a fermentation process according to the present technology.

Figure 7:
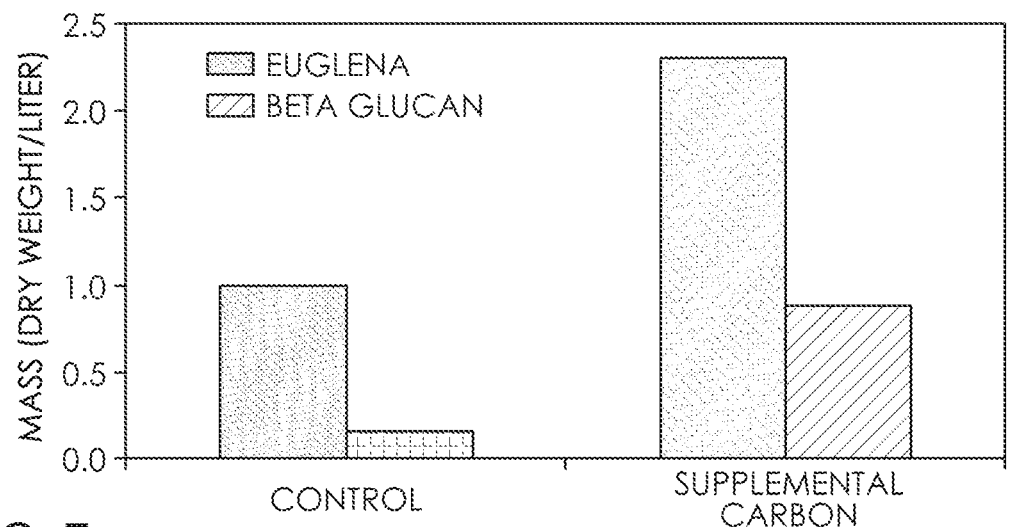

FIG. 7 graphically depicts the mass in dry weight per liter of *Euglena* and beta glucan grown in a control media and a media having a supplement carbon treatment.

Figure 8:
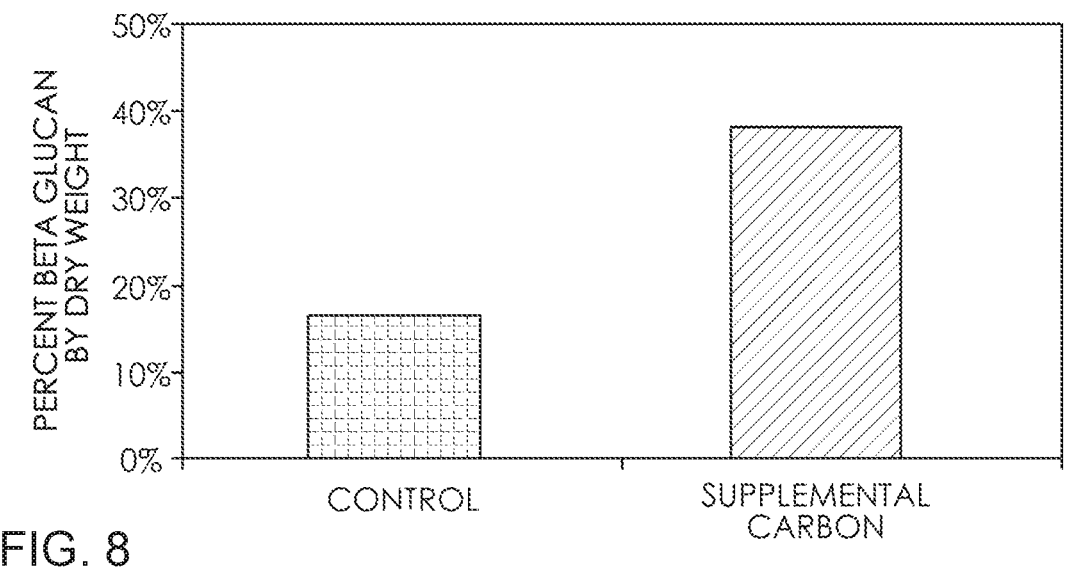

FIG. 8 graphically depicts the percent beta glucan by dry weight of *Euglena* grown in the control media and the media having the supplemental carbon treatment.

Figure 9:
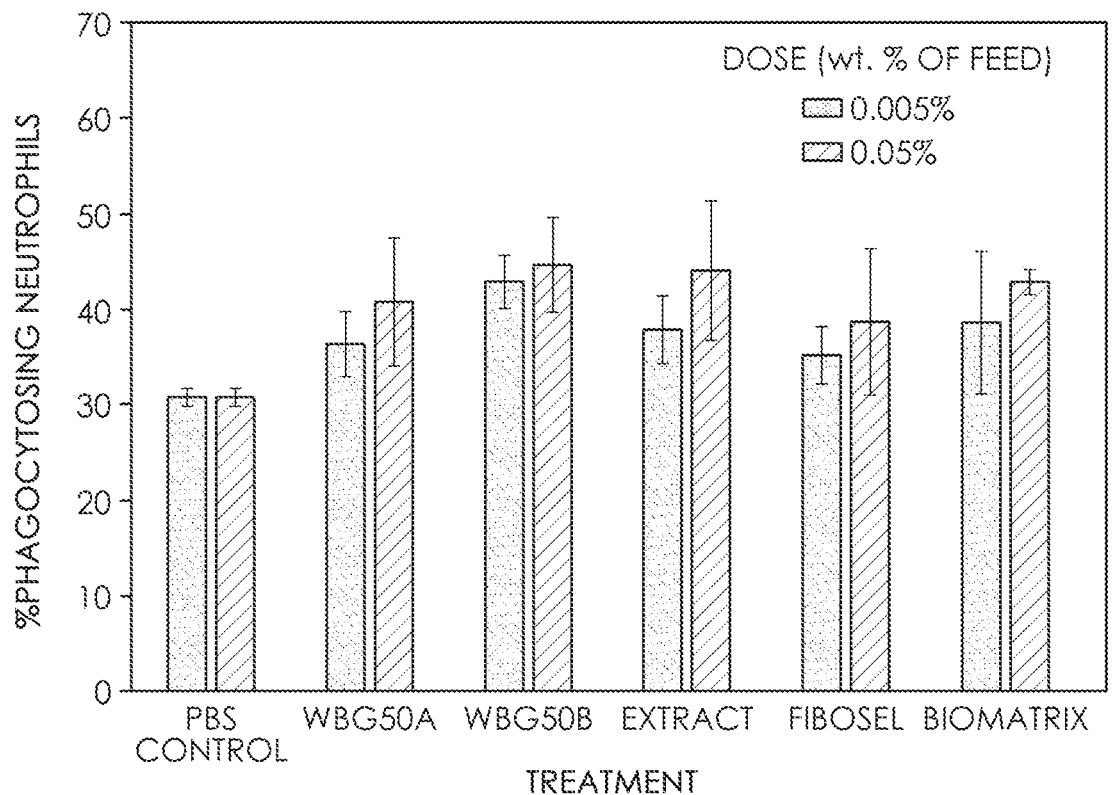

FIG. 9 graphically depicts the phagocytosis index of mouse neutrophils sampled from peripheral blood 48 hours after being fed heterotrophically grown paramylon. Commercial yeast beta glucan products, i.e., Fibosel (Trouw Nutrition, Highland, Ill.) and Macrogard (Orffa Inc., Henderson, Nev.), were compared to dried heterotrophically-produced *Euglena* cells (WBG50) and paramylon extracted from said cells. Bars represent means (±SE), (n=3 mice).

Figure 10:
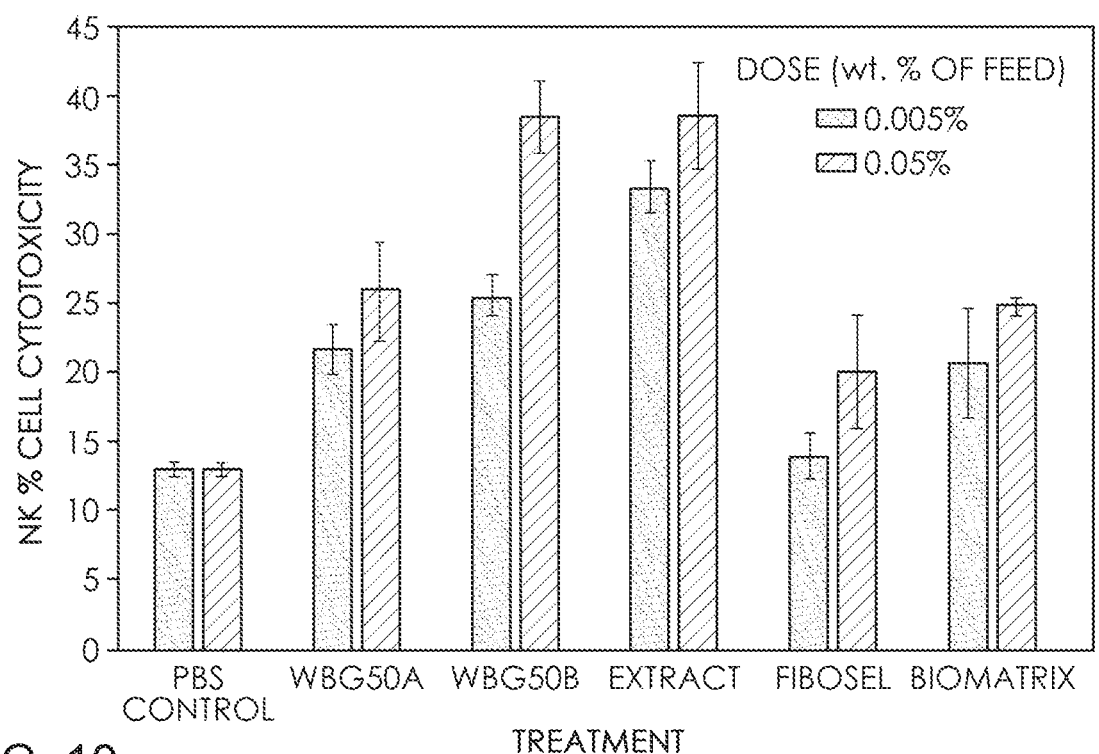

FIG. 10 graphically depicts natural killer (NK) cell activity of spleen cells harvested 48 hours after being fed heterotrophically grown paramylon. Commercial yeast beta glucan products (Fibosel, Macrogard) were compared to dried heterotrophically-produced *Euglena* cells (WBG50) and paramylon extracted from the cells. Bars represent means (±SE), (n=3 mice).

Figure 11:
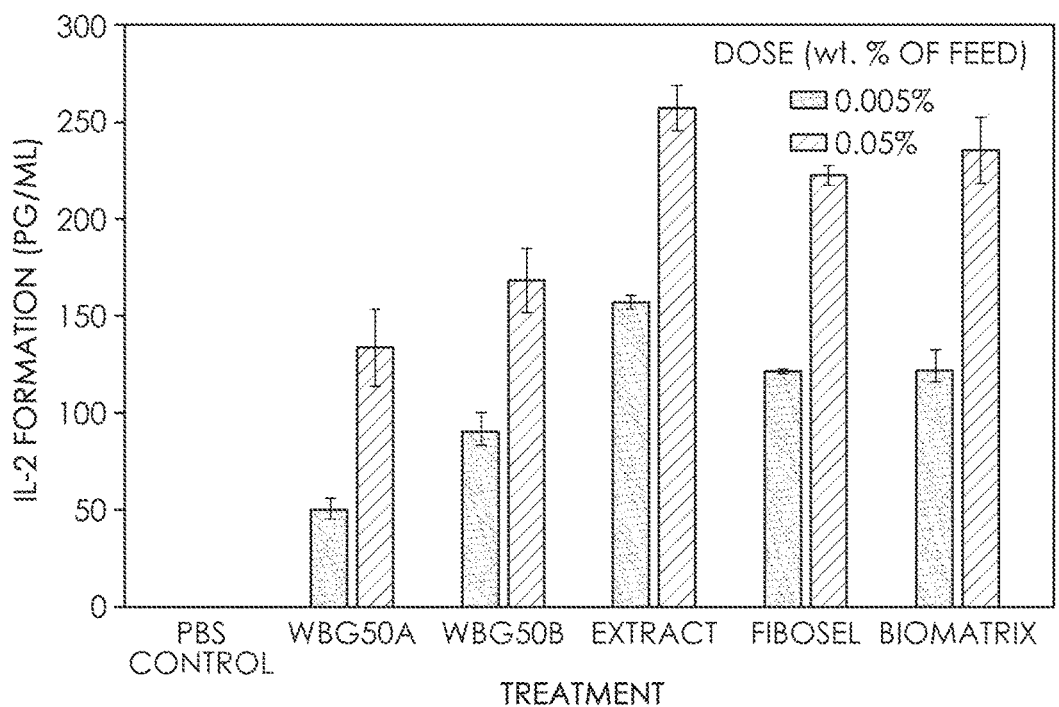

FIG. 11 graphically depicts IL-2 (cytokine) formation (by ELISA) in mice 48 hours after being fed heterotrophically grown paramylon. Commercial yeast beta glucan products (Fibosel, Macrogard) were compared to dried heterotrophically-produced *Euglena* cells (WBG50) and paramylon extracted from said cells. Bars represent means (±SE), (n=3 mice)

Figure 12:
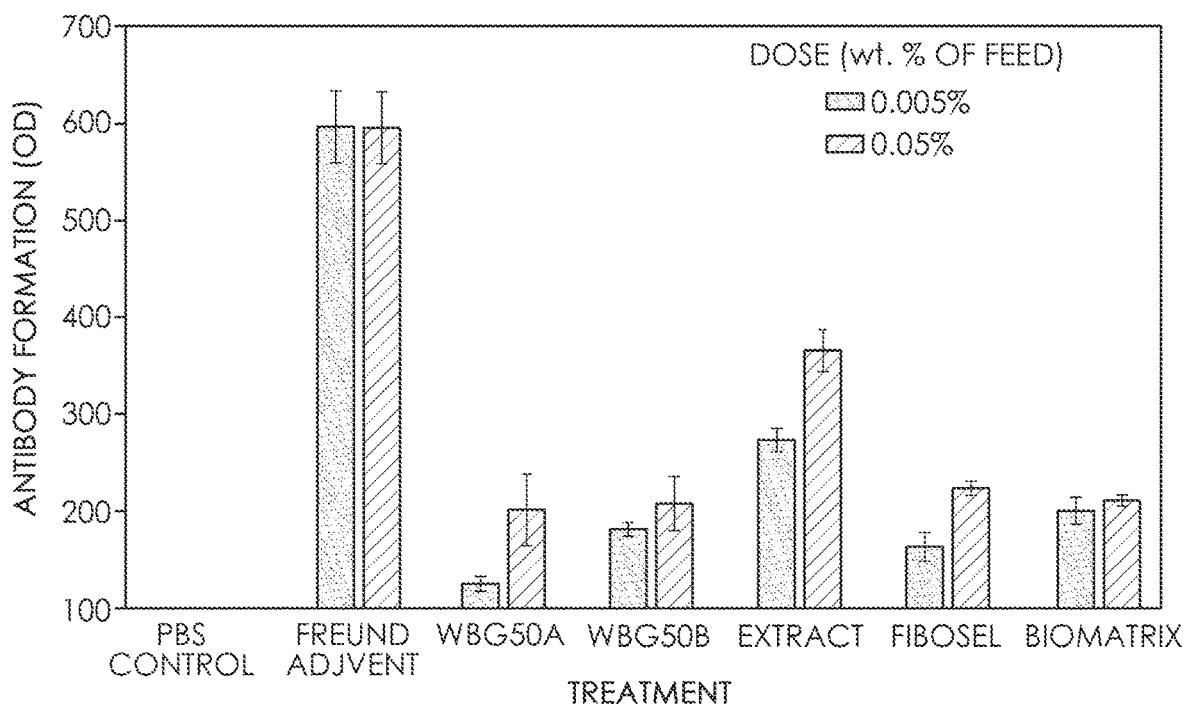

FIG. 12 graphically depicts antibody formation following ovalbumin injection and daily dosing of heterotrophically grown paramylon. Commercial yeast beta glucan products (Fibosel, Macrogard) were compared to dried heterotrophically-produced , *Euglena* cells (WBG50) and paramylon extracted from said cells. Bars represent means (±SE), (n=3 mice).

Figure 13:
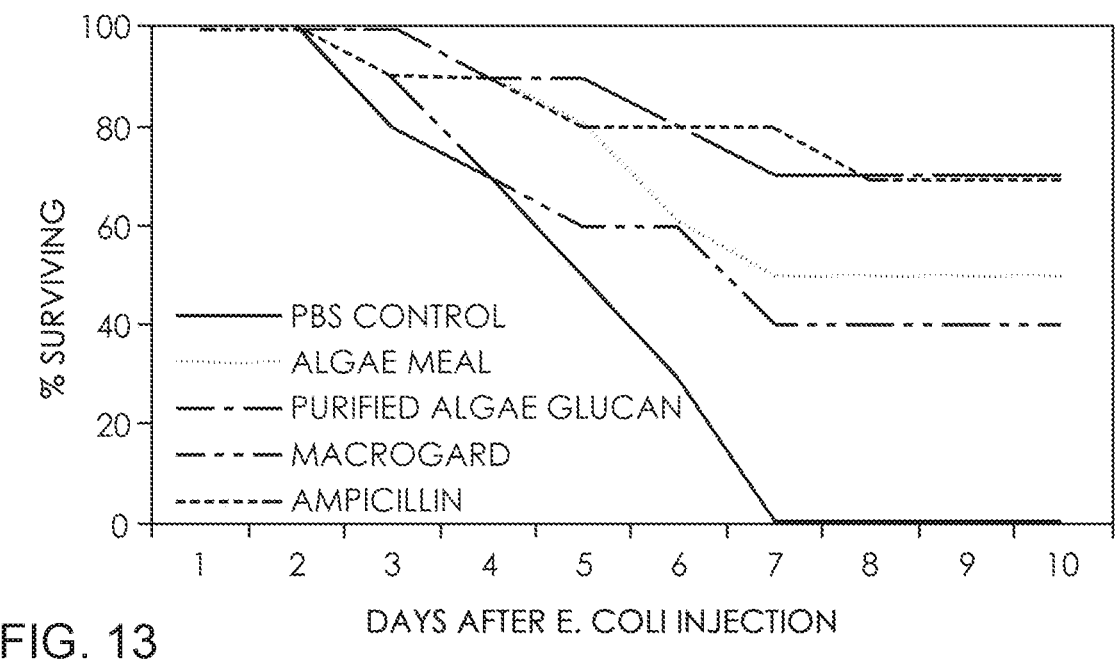

FIG. 13 graphically depicts survivorship of mice following an injection of *E. coli* on day 0. Algae meal, purified algae beta glucan, and Macrogard yeast beta glucan extract were fed orally by gavage for 5 days at a dose equivalent to 0.01% of the daily feed ration starting 2 days before the *E. coli* injection (day—2). The PBS control group was given just a PBS gavage while the antibiotic treatment group was given 13 mg/kg of Ampicillin orally on days 0 through 4. (n=10 mice per treatment group).

Figure 14:
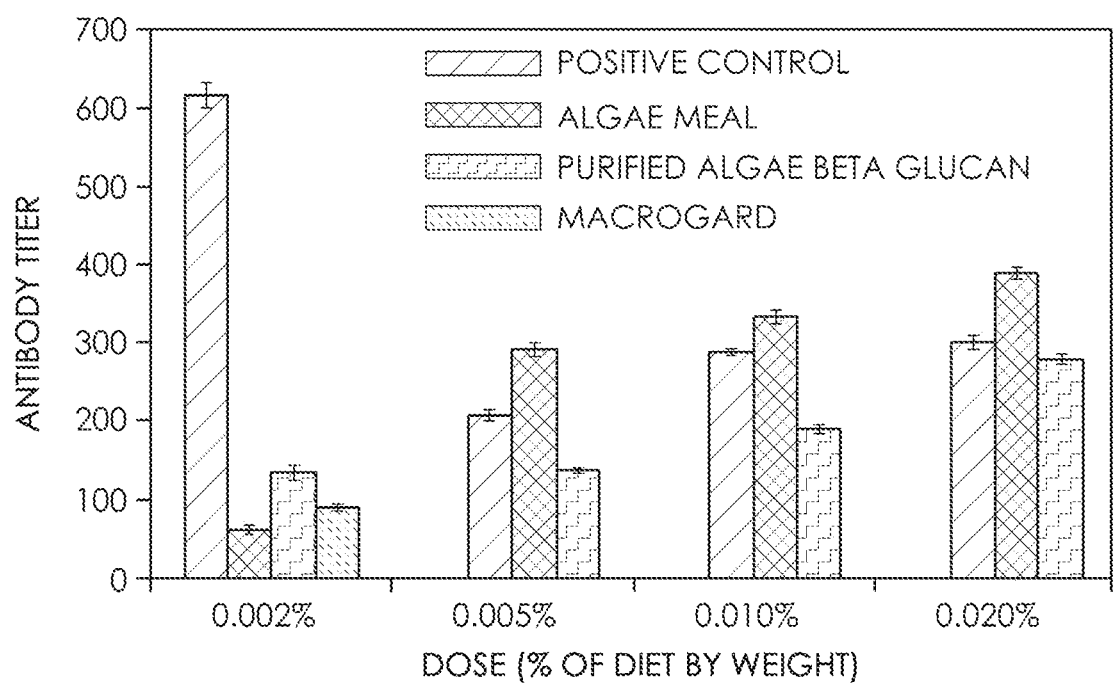

FIG. 14 graphically depicts antibody formation following ovalbumin injection (day 3 and 16) and daily dosing of beta glucan treatments for 23 days. Bars represent means±standard error. n=3 mice per treatment group.

Figure 15:
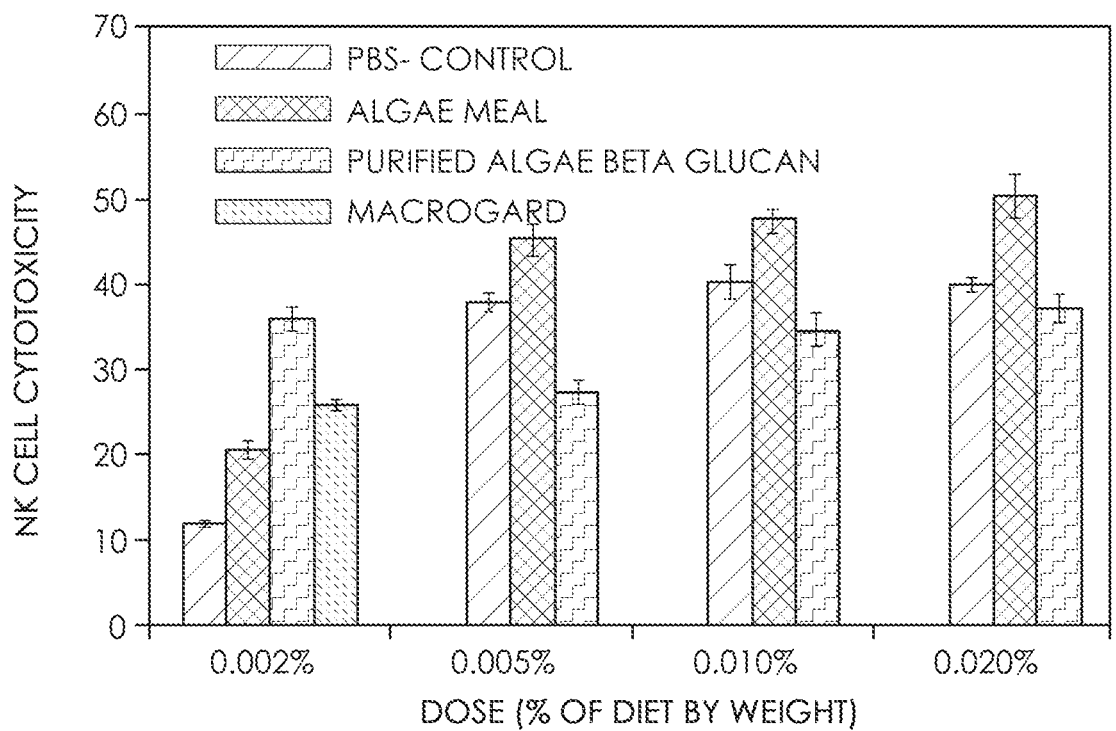

FIG. 15 graphically depicts Natural Killer (NK) cell activity of spleen cells harvested on day 14. Bars represent means±standard error. n=3 mice per treatment group.

Figure 16:
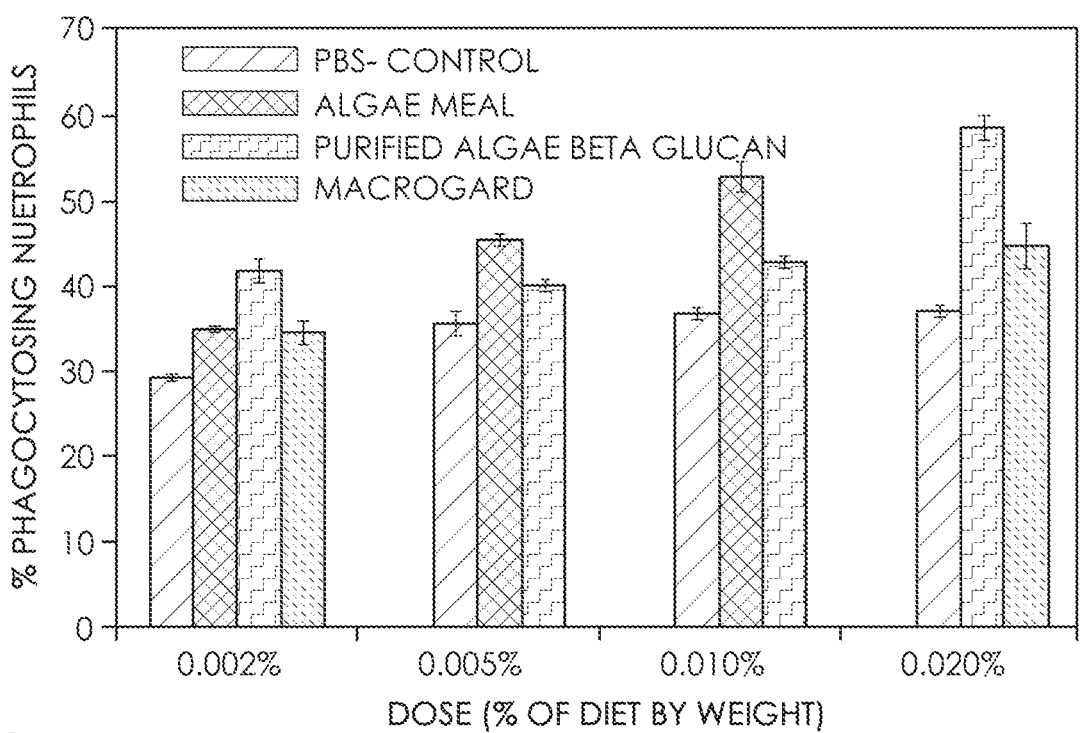

FIG. 16 graphically depicts the phagocytosis index of mouse neutrophils sampled from peripheral blood on day 14. Bars represent means±standard error. n=3 mice per treatment group.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom, Regarding the methods disclosed, the order of the steps presented is exemplary in nature, and thus, the order of the steps can be different in various embodiments. Except in the examples, or where otherwise expressly indicated, all numerical quantities in this description indicating amounts of material or conditions of reaction and/or use are to be understood as modified by the word "about" in describing the broadest scope of the technology.

The present technology relates to beta glucan, including beta glucan derived from *Euglena*, and uses thereof. Compositions containing *Euglena* derived linear beta-1,3-glucan can be orally administered to promote immune system health, prevent disease, reduce mortality, reduce the effects of stress, increase growth rates, or improve feed conversion efficiency in animals. Various commercially raised animals, such as mammals, fish, birds, and crustaceans, can be treated. Dosages or feed inclusion rates can vary depending upon the animal species that is administered the beta glucan. In certain embodiments, the beta-1,3-glucan can comprise less than 1% of the total feed. Animals can also be treated at any stage of life, although animals that are raised for the purpose of breeding are often considered to be more valuable and therefore it may be considered to be more economical to treat these animals. The present technology is intended to include compositions, use of the compositions, and various methods as described herein to enhance the well-being of animals. Methods used to prepare such compositions are also included in the present technology.

Carbohydrate Branching Structure

With reference to FIGS. 2, 3, and 4, aspects of various beta glucans from various sources are shown. The beta glucan produced by Euglenoids is unique in its physical characteristics and is often referred to as "paramylon." Paramylon consists of a linear polymer that is almost exclusively beta-1,3 glucan with very few side branches. This structure differs significantly from the yeast-derived beta glucans that have been studied most intensively and commercialized for immune support applications, Yeast beta glucans contain a beta-1,3 glucan backbone that is substituted with beta-1,6 side chains (2-3 glucose units long) every 10-30 glucose units. The unbranched nature of paramylon is an important distinction compared to other sources of beta glucans when considering its use in immune support applications, After isolating paramylon from whole *Euglena* cells, a linkage analysis was performed to determine the relative amounts of each type of bond between glucose monomers. For glycosyl linkage analysis, the sample was permethylated, depolymerized, reduced, and acetylated; and the resulting partially methylated alditol acetates (PMAAs) were analyzed by gas chromatography-mass spectrometry (GC-MS) as described by York et al. (1985) Methods Enzymol. 118:3-40. Initially, dry sample was suspended in about 300 μl of dimethyl sulfoxide and placed on a magnetic stirrer for 1-2 weeks. The sample was then permethylated by the method of Ciukanu and Kerek (1984) Carbohydr. Res. 131:209-217 (treatment with sodium hydroxide and methyl iodide in dry DMSO). The sample was subjected to the NaOH base for 10 minutes then methyl iodide was added and left for 40 minutes. The base was then added for 10 minutes and finally more methyl iodide was added for 40 minutes. This addition of more methyl iodide and. NaOH base was to insure complete methylation of the polymer. Following sample workup, the permethylated material was hydrolyzed using 2 M trifluoroacetic acid (2 h in sealed tube at 121 C), reduced with NaBD4, and acetylated using acetic anhydride/trifluoroacetic acid. The resulting PMAAs were analyzed on a Hewlett Packard 5975C GC interfaced to a 7890A MSD (mass selective detector, electron impact ionization mode); separation was performed on a 30 m Supelco 2330 bonded phase fused silica capillary column.

TABLE 2

Linkage Analysis of 2 Paramlyon Samples Extracted from *Euglena gracilis*.

| GLYCOSYL RESIDUE | Sample 1 | Sample 2 |
|---|---|---|
| terminally-linked glucopyranosyl residue (t-glc) | 0.34 | 0.3 |
| 3-linked glucopyranosyl residue (3-glc) | 93.03 | 94.1 |
| 4-linked glucopyranosyl residue (4-glc) | 2.25 | 2.4 |
| 2,3-linked glucopyranosyl residue (2,3-glc) | 3.47 | 2.3 |
| 3,6-linked glucopyranosyl residue (3,6-glc) | 0.36 | 0.8 |
| 2,3,4-linked glucopyranosyl residue (2,3,4-glc) | 0.55 | 0.1 |
| Total | 100.0 | 100.0 |

This linkage analysis indicates that both paramylon samples are mainly composed of 3-linked glucopyranosyl residues. For example, the beta glucan can be greater than about 90% unbranched beta-(1,3)-glucan, and in some cases can be greater than about 93% unbranched beta-(1,3)-glucan or greater than about 94% unbranched beta-(1,3)-glucan. Minor amounts of 4-linked and 2,3 linked glucopyranosyl residues were found along with negligible amounts of 3,6-linked, terminal and 2,3,4-linked glucopyranosyl residues. These data confirm that paramylon is comprised mostly of a linear, unbranched beta 1,3 glucan. According to several studies, beta-1,3 glucan is the form of beta glucan that actually binds to receptors on the surface of immune system cells, such as Dectin-1 (a major receptor on immune system cells like macrophages) and complement receptor 3. Following the uptake of particulate paramylon and its digestion into smaller fragment by macrophages, the high proportion ofbeta-1,3 glucan in paramylon relative to yeast-derived beta glucans may result in improved immune system modulation. For example, immune system activation may be improved with increasing doses of paramylon whereas efficacy may diminish with higher doses of yeast-based beta glucans, possibly due to the presence of beta-1,6 side chains that stereometrically interfere with one another and hinder access to the Dectin-1 receptor.

Three-Dimensional Structure

The three-dimensional structure and folding ofbeta-1,3-glucan can affect the bioavailability, surface area, and overall efficacy in immune stimulation applications. In linear, beta-1,3-glucan chains, the structure is governed by the glycosidic linkage pattern. Because the chair-form ring of glucopyranosyl is rather rigid, most of the flexibility of the glucan chain arises from rotations around the bonds of the glycosidic linkages. X-ray crystallography and spectroscopy techniques indicate that linear glucans have a triple-helix backbone in the solid state. Paramylon that is produced by *Euglena* is considered to be one of the structurally most simple of the beta glucans, with few glycosyl side chains, This is in direct contrast to laminaran, lentinan, scleroglucan, schizopylann and yeast-derived beta glucans that have 1,4 or 1,6-linked side chains exposed toward the exterior of the helical structure.

The triple-helix structure of linear beta-1,3-glucan is stabilized by ree types of hydrogen bonding:
1. Intermolecular hydrogen bonding formed between the different chains in the same x-y plane;
2. Intramolecular hydrogen bonding formed between adjacent O atoms in the same chain; and
3. Intermolecular hydrogen bonding formed between different chains in a different x-y plane.

The triple helix structure is stable over a broad range of temperatures at a neutral pH, resulting in a polymer that is water insoluble. However, the hydrogen bonds can be destabilized by various means to change the conformation of the paramylon polymer. For example, paramylon can be dissolved in alkaline solutions (typically 0.2 M NaOH or stronger), aprotic polar solvents like DMSO, in the presence of strong chaotropic agents (e.g., urea), or by increasing temperatures above the triple-helix melting temperatures (~135° C.). Different immunological effects can be obtained that are related to the beta-1,3-glucan conformation, be it the native state, denatured, or denatured and re-natured. Beta-1,3-glucan in any of these three conformations can serve as the building block for additional reactions that add or improve its functionality. Several of these modifications to produce functionalized beta-1,3-glucans and some of their respective applications are discussed herein. The conformation of the beta glucan and its resulting solubility may also affect how it is delivered; for example, water soluble beta-1,3-glucan can be directly injected whereas particulate beta glucan is more suitable for oral administration.

Particle Size, Molecular Weight, and Surface Area

The particle size, molecular weight, and surface are all factors that affect the function and bioavailability of the beta-1,3-glucan particle, In general, it can be preferable to have a beta-1,3-glucan particle between 0.2 and 5 microns in diameter with a high surface area to maximize interactions with immune cells. After absorption at the gut associated lymphoid tissue (GALT) or following injection, the beta-1,3-glucan particle is ingested and cleaved by macrophage cells. Macrophage cell size varies between species. For example, hamster and rat aveolar macrophage diameters average about 13.6 and 13.1 microns, respectively, with macrophages from monkeys averaging 15.3 microns and macrophages from humans averaging 21.2 microns. The particle size of the beta-1,3-glucan molecule should be the appropriate size to maximize uptake at the GALT and also into the macrophages. The ideal particle size may differ between species. Macrophage cells can vary in size between different organisms, which may explain a portion of the variability between optimal beta-1,3-glucan particle sizes.

The molecular weight of a beta glucan substance is known to affect the effectiveness of the compound in immune stimulation applications. Beta-1,3-glucans produced by Euglenoids can typically have a molecular weight of about 200-500 kDa.

TABLE 3

Sources of Beta Glucans, Structures, and approximate Molecular Weights.

| Name | Source | Native Form Solubility | Structure | Molecular Weight (kDa) |
|---|---|---|---|---|
| Glucan from Euglenoids | Algae | Particulate | β-(1,3) unbranched | 200-500 |
| Glucan from Saccharomyces | Yeast | Particulate | β-(1,3) β-(1,6) branched (30:1) | 200 |
| Curdlan | Gram negative bacteria | Particulate | β-(1,3) unbranched | 50-200 |
| Laminarin | Brown seaweeds | Soluble | β-(1,3) with some β-(1,6) branching (30:1). The β-(1,6) side chains are composed of two glucose units. | 7.7 |
| Scleroglucan | Fungus | Soluble | β-(1,3) β-(1,6) branched (6:1). The β-(1,6) side chains are composed of two glucose units. | 1020 |

Level of Purity of Beta-1,3-Glucan

The level of purity of a beta glucan compound has been determined to have an effect on efficacy, possibly stemming from other material present that inhibits the interaction between the beta glucan and immune cells. Using the methods described herein, paramylon can be easily isolated in the form of granules from Euglenoid cells. As a result, the purity of paramylon is very high relative to common preparations of beta glucans from yeast and other organisms. Using the methods described herein, purity levels greater than 98% (measured by an enzymatic assay which detects beta glucan, Megazyme) can be obtained. In comparison, the highest-grade yeast-derived beta glucans can rarely achieve greater than 90% purity and several commercial products in the animal feed industry specify only about a 35-60% purity. Moreover, achieving high purity beta-1,3-glucan can be achieved more cost-effectively than with yeast-derived glucans due to the ease of separation resulting from the lack of a cell wall in Euglenoids and easy recovery of paramylon granules. Finally, since no harsh chemicals (e.g., strong acids and bases) are required to recover the paramylon granules, the beta glucan can be recovered in its native form without modifying its chemical composition and configuration. In some cases, the use of pure, unmodified paramylon can be advantageous in comparison to solubilized and modified paramylon or beta glucans obtained from other organisms that are modified during the extraction process.

Method for Production of Paramylon in *Euglena gracilis*

*Euglena* sp. may be grown in a controlled environment, such that the *Euglena* remain the dominant microorganism in the environment. This is not easy to achieve, as other organisms are typically capable of competing for the same biological resources (e.g., nutrients, micronutrients, minerals, organic energy, and/or light), Many of these microorganisms typically have a faster growth rate and are capable of out-competing *Euglena* absent several controlled growth mechanisms that favor *Euglena* sp. These growth mechanisms can include one or more methods such as employment of growth media that favors *Euglena*, operation at a temperature that favors *Euglena*, addition of acids and bases that favor *Euglena*, addition of compounds that are toxic to competing organisms other than *Euglena*, selective filtration or separation of *Euglena*, and addition of micro-predators or viruses that control the populations of organisms that are not *Euglena*. All of these methods affect the growth rate and the ability of *Euglena* to convert energy into beta glucan.

In order to achieve a sufficient population of the algae or protist, the organism can also be grown in large aerobic fermentation vessels that are similar to those vessels used to grow yeast. In some embodiments, these vessels may be non-pharmaceutical grade vessels used in the commercial production of lysine, or other amino acids or proteins using *Saceharemyces* sp., *Eschericia coli*, or other microorganisms.

The conversion of energy to bioavailable beta glucan may be enhanced by the addition of an organic carbon source to the *Euglena* growth media, by the selective addition of light, or by both. Again, these aspects affect the ability of *Euglena* to compete with other organisms. In general, *Euglena* that are grown in an uncontrolled environment will not display the same beneficial properties of high beta glucan concentration, fast growth rates, and efficient production of beta glucans that *Euglena* produced in a more controlled growth environment will display.

The growth of high concentrations of beta glucan-containing *Euglena* reduces the cost of beta glucan production in several ways, including the following. First, the beta glucan containing compounds are not contained in the cell wall of the organisms and do not require elaborate and/or expensive fractionation methods or extraction processes. Second, the *Euglena* organisms are relatively large and may be separated from water relatively quickly by employing a centrifuge, filter, or other separation device. Third, individual *Euglena* cells are composed of a larger percentage of beta glucan (as a percent of total cell mass) in comparison to other organisms, which results in high rates of conversion of organic sugars to beta glucan and easier recovery of the beta glucan. Fourth, aglow are capable of heterotrophic and photosynthetic metabolisms, and therefore can convert free energy, in the form of light, into valuable beta glucans. Fifth, beta glucans produced from *Euglena* are not totally identical to other beta glucans. However, in some embodiments the *Euglena* derived beta glucans can be used in combination with other beta glucans (e.g., yeast derived beta glucans) in order to provide immune modulation properties.

Beta glucans from *Euglena* have not been studied as thoroughly as those from yeast. The extent that *Euglena* derived beta glucans modulate the immune system can be compared with yeast derived beta glucans. Experiments comparing *Euglena* derived beta glucans and yeast derived beta glucans are described in the Examples contained herein.

In their native state, yeast-derived glucans are present in lower purity compositions and are also bound into the cell wall to other molecules that may have either a stimulatory or inhibitory effect. Yeast-derived beta glucans also contain 1,3;1,6 branching that is not present in *Euglena*-derived glucans. Because yeast-derived beta glucans require extraction, it is likely that the extraction may result in additional modifications to the three-dimensional structure of the beta glucans, such as by cleaving portions of the beta glucans or by winding or unwinding helical coils or other structures.

Beta glucans from different sources can vary in terms of backbone structure, branching linkages; frequency and length, molecular weight, and other features. Research presented at the National Cancer Institute Conference demonstrated that even slight variations in these characteristics can affect bioactivity (see the online document available at: www.immunehealthbasics.com/GlucaStructureNR.html).

For example, in an in vivo anti-tumor study, beta-1,3;1,6-glucans from three separate sources with similar primmy structures were combined with a monoclonal antibody in a lymphoma model.

One form of beta-glucan that is commercially available is WellMune™ (Biothera Corporation, Eagan, Minn.), which is derived from yeast. Another form ofbeta-glucan also produced using yeast is available from BioTec Pharmacon (Norway), marketed as Macrogard by Immunocorp (Norway).

Extraction of Beta Glucans from *Euglena gracilis*

The beta glucan may be extracted from the algae or protist cell through a liquid-solid separation, a physical separation method, or another method. The resulting purified beta glucan compound may undergo additional reactions in order to improve the binding affinity, or to alter the binding affinity for a specific purpose. For example, sulfated polysaccharides have shown to be effective in treating HIV (Damonte, Elsa B, Matulewicz, Marfa C., Cerezo, Alberto S; Current Medial Chemistry; 2004). Sulfated beta glucans from algae or protist sources may demonstrate similar efficacy. Additional process that may be used to alter the structure of the beta glucan compound in order to increase or alter the efficacy of immune system stimulation are phospholylation, acetylation, and amination.

Method of Oral Administration

The beta glucans from *Euglena* may also be added to the diet of animals following isolation from the *Euglena* cells. Simple procedures to lyse the *Euglena* cells and concentrate the beta glucan can achieve a product that can exceed 75% purity of beta glucan. This isolated product has the benefit of being more concentrated, having lower protein content to reduce allergic reactions, and also permits a longer shelf life. This isolated product can be incorporated into diets of animals in order to achieve a target beta glucan dosing, or in the case of various aquaculture applications, the beta glucan can be added to the water directly in the form of particles or feed pellets where it is ingested by the target aquaculture species.

In some embodiments, the present technology can stimulate a macrophage response using *Euglena* derived beta glucans. Stimulation of the macrophage response is known to activate a cytokine pathway that promotes enhanced general immune system activity. Such a response may be desirable for prevention of infections, treatment of tumors and cancers, or to support a compromised immune system, as would be expected in an immune deficiency syndrome, a patient undergoing surgery or chemotherapy, or a patient with severe burns. The beta glucans may be administered orally, injected, using a nasal spray, or as a topical ointment or cream. The beta glucan may be administered continually or during specific times when the immune system may be challenged, such as when an organism is young, is stressed, or is about to undergo surgery or another operation. A period of stress may occur during a transfer to a new environment, inclusion in a larger or new population of organisms, or when an organism is about to undergo something that could be challenging to its immune system.

Feed Compositions:

Feed compositions typically vary between species. Different feed compositions are also given to the same species for different purposes and at different life stages.

Dosing:

The amount of beta glucan to be added as a feed supplement can range between 0.001% to 2% of the total mass of the feed, as measured by dry weight analysis.

TABLE 4

Examples of Beta Glucan (BG) Dosing Percentages.

| | Low | Preferred | High |
|---|---|---|---|
| Perfect of feed (% of daily feed that is BG) | 0.01% | 0.10% | 1% |
| Daily food consumption, as % of body mass | 0.50% | 2.00% | 5% |
| Daily BG consumption, as % of body mass | 0.00005% | 0.00200% | 0.0500% |

Exact dosing levels of algae or protist-derived beta glucans in an animal food composition can depend on the beta glucan percentage and efficacy, the organism, and the dosing schedule.

One example of an animal feed application is to feed *Euglena* derived beta-glucan to swine. In this example, *Euglena gracilis* can be grown heterotrophically in a controlled environment (through the manipulation of carbon source, nutrient levels, pH, temperature, and other factors), centrifuged or filtered to remove it from the water, and dried. The exact conditions of growth, as well as additional factors such as lighting and the addition or removal of molecules can affect the ultimate beta glucan composition, structure, and relative abundance (by mass). The resulting algae meal can be mixed directly into an animal food composition to be fed to the swine. The beta glucan supplement can be incorporated into the feed composition and fed to the swine multiple times per day, daily, or less frequently.

As described, *Euglena gracilis* that is grown heterotrophically can be added to the animal feed composition for swine. When dosed properly and fed according to a proper schedule, this can have a beneficial on the animal's overall well-being, as may be measured by increased survival rates, increased growth rates, increased feed conversion efficiency. Alternatively, effects on the immune system may be measured directly by measuring indicating factors such as ADO, ADFI, G:F, the lymphocyte proliferation index, cytokine levels, cortisol levels, tumor necrosis factor-alpha, or IL-10. In a controlled experiment, the addition of algae or protist meal containing active P-1,3 glucans may demonstrate statistically significant differences in one or more of these factors between the control or experimental groups. Experiments illustrating such measurements are found in the Examples provided herein. The addition of *Euglena gracilis* to the animal food composition in the correct dosing levels can affect these biochemical indicators and provide a beneficial effect on the well-being of the organism.

Other applications include adding the *Euglena* derived beta glucan to a feed composition that is fed to poultry, cows, fish, shrimp, horses, dogs, cats, reptiles, birds and other animals, including valuable or exotic animals kept at zoos or in aquariums.

Examples of ingredient combinations for selected applications:

When combined into animal feed, the *Euglena* derived beta glucan may be combined at a range of dosing levels, but generally this level can be between 1:10,000 and 1:500 by dry weight. Specific ingredient combinations may differ between organisms, life stages, and the desired outcomes. Additionally, *Euglena* derived beta glucans can be combined with other immune-stimulating ingredients in order to provide the maximum immune stimulation benefits. Example ingredient combinations are listed below for poultry, swine, and canine applications. Algae or protist-derived may be combined with any combination of (but not limited to) these ingredients in order to make an animal feed product.

There are many animal feed ingredients that may also benefit from combination with beta glucan. Common animal feed components, for example, can include one or more of the following ingredients: corn meal, dehulled soybean meal, wheat middlings, limestone, monocalcium-dicalcium phosphate, salt, manganous oxide, manganese sulfate, zinc oxide, ferrous sulfate, copper sulfate, cobalt carbonate, calcium iodate, sodium selenite, vitamin A, vitamin D, vitamin E, Menadioane sodium bisulfate complex (source of vitamin K complex), riboflavin supplement, niacin supplement, calcium pantothenate, vitamin 1312, d-biotin, thiamine mononitrate, pyridoxine hydrochloride, folic acid, methionine, soybean oil, mineral oil, amino acids, Chicken, calcium, phosphoms, chrondrotin, glucosamine, Omega 3 & Omega 6, beet pulp, DHA (from fish oil), beta carotene, fish meal, Vitamin blend, alpha-linlenic acid, amino acids, arachidonic acid, ascorbic acid, beef, biotin, brewers yeast (dried), calcium carbonate, cellulose, chelated minerals, chondroitin sulfate, cobalt, copper, corn meal, corn oil, di calcium phosphate, DL-methionine, docosahexaenoic acid, dried egg product, durum flour, ethoxyquin, fat, carbohydrate, ferrous sulfate, fiber, fish meal, fish oil, flax meal, folic acid, frnctooligosaccharides, gelatin, glucosamine hydrochloride, glycerin, ground barley, ground corn, ground sorghum, guar gum, inositol, iodine, iron, Kangaroo, lamb, l-carnitine, linoleic acid, lutein, magnesium, magnesium oxide, manganese, marigold extract, mannanoligosaccharid.es, minerals, mixed tocopherols, monosodium phosphate, niacin, marigold. extract, blueberries, dried kelp, phosphoms, potassium, potassium chloride, potassium iodide, potassium sorbate, protein, pyridoxine hydrochloride, riboflavin, rice, rice flour, rosemary, rosemary extract, tapioca starch, taurine, thiamine mononitrate, titanium dioxide, vitamin A, vitamin B-1, vitamin B12, vitamin B-2, vitamin B-6, vitamin C, vitamin D3, vitamin E, vitamin K, water, wheat, wheat glutens, xanthan gum, zinc, zinc oxide, zinc sulfate, any of the ingredients presently listed by the Association of American Feed Control Officials, and combinations thereof.

Additional ingredients for enhancing immune system activity:

The following ingredients are related to enhanced immune system performance and can be combined with *Euglena* derived beta glucans or meal in order to achieve the effects of enhanced immune system activity: vitamin C, alfalfa, flax seed, parsley, cranberries, spirulina, chlorella, vitamin A, vitamin E, copper, zinc, chromium, iron, arginine, alklyglcerol, coenzyme QIO, dimethglycine, phytonutrients, beta carotene, essential oils, fish oils, spices and their derivatives, and combinations thereof.

The ingredients above may be used in various applications and for feeding various organisms. For example, the ingredients listed herein as animal feed components may also be combined with algae or protist-derived beta glucans for dog, cat, poultry, aquaculture and other feed applications, In addition to the immune stimulation benefits of *Euglena* derived beta glucans, the additional algae biomass may be incorporated. In particular, *Euglena gracilis* or another species may be grown such that relatively high concentrations of valuable DHA, Omega 3 fatty acid, Omega 6 fatty acid, and tocopherols are also added to the feed composition.

Additional Compositions

Although beta glucan can be beneficial when included with one or more feed ingredients, there may be certain synergistic effects when beta glucan is fed in combination with one or more additional substances. For example, beta glucan may be fed in combination with probiotics such as *Bacillus licheniformis* or *Bacillus subtilis* to provide a synergistic effect. In this embodiment the up-regulation of the immune system may help the body to naturally fight invasive pathogens while the probiotics maintain a healthy intestinal flora that are more stable to overturn. Beta glucan that is fed in combination with other types of non-digestible fibers (e.g., prebiotics) may also exhibit a synergistic effect. Examples of prebiotics that may be beneficially combined with beta glucan include but are not limited to fructooligosacchaddes (FOS), lactulose and mannan oligosaccharides (MOS). Prebiotics combined with beta glucan may be derived from yeast, micro-algae, grains, kelp, other terrestrial plants, and other sources. Other substances that may be beneficial in combination with beta glucan include vitamin C, vitamin E (specifically RRR alpha tocopherol), carotenoids (Astaxanthin, beta-carotene, lutein, zeaxanthin), DHA or EPA fatty acids, trace metals (iron, magnesium, lithium, zinc, copper, chromium, nickel, cobalt, vanadium, molybdenum, manganese, selenium, iodine), halquinol, ME Detoxizyme, vitamin D3, ascorbic acid, and dietary minerals (calcium, phosphorus, potassium, sulfur, sodium, chlorine, magnesium, boron, chromium). Beta glucan may also be fed in combination with other enzymes, which may improve the bioavailability or digestibility of one or more nutrient sources in the feed. In some cases, beta glucanase may be provided as an enzyme in the feed to cleave the beta glucan into smaller, more digestible fragments or to release the metal from a metal beta glucan complex. In some embodiments, one or more of these additional substances can be included in the residual algae meal, which may be cultivated with the intent of increasing the concentration of the synergistic substances.

Further ingredients can be combined with beta glucan and the various beta glucan compositions described herein. These include an additional immune modulating, stress reducing, or other stimulant ingredient selected from the group consisting of alpha tocopherol, cholecalciferol, zinc, chromium, selenium, arginine, ascorbic acid, alklygicerol, caffeine, kava kava, curcuma longa, spirulina, calcium D-glucarate, coenzyme Q10, peptides, dimethglycine, docosahexaenoic acid, ecosapentaenoic acid, alpha-lineolenic acid, astaxanthin, beta carotene, lutein, lactobacillus probiotics, bifidobacterium probiotics, mannoliggosaccharide, fmctooliggosaccharides, Astragalus, Echinacea, Esberitox, garlic, glutathione, kelp, L-arginine, L-ornithine, lecithin granules, extracts from maiitake, reishi or shiitake mushrooms, manganese, quercetin, bromelain, Olive Leaf, Sambucus, Umcka, panthothenic acid, quercetin, alpha lipoic acid, essential oils, fish oils, spices and their derivatives, pterostilbene, and combinations thereof.

Complexes with Trace Metals

In some embodiments, beta glucan can be complexed with a trace metal in order to create a complex that simultaneously be used to improve trace metal bioavailability while promoting general immune system activity. Trace metals include copper, zinc, iron, cobalt, magnesium, molybdenum, manganese, and combinations thereof. The beta glucan and trace metal complex can be the result of complexing a soluble, inorganic trace metal salt with a beta glucan in solution.

The beta glucan polysaccharide can comprise either a bioavailable form of beta glucan, such as paramylon granules that are present in a dry or wet whole cell algae suspension or beta glucan present in a dry or wet whole cell yeast, or an extracted source of beta glucan from algae, yeast, or another organism. The polysaccharide can be comprised of a suspension or paste of *Euglena gracilis* that has been grown heterotrophically in one or more sterile bioreactors. The *Euglena* can also be grown in an optimal manner such that the beta glucan p01lion of the algae product comprises greatel than 20% of the algae biomass, as measured on a dry weight basis. Examples of processes for growing and creating such products are illustrated in FIGS. 5 and 6, With reference to FIG. 5, an embodiment of a fermentation process is shown. Algae biomass is produced in a fermenter (1) under sterile conditions on chemically defined media. After the desired amount of time in the fermenter (1), the fermenter broth is transferred to a centrifuge (2) that dewaters the broth to produce two process streams: a wet algae meal that contains about 75% moisture; and used media. The wet algae meal contains a mixture of whole algae cells, algae cell fragments, and polysaccharides granules. The wet algae meal can be a polysaccharide solution containing over 50% by dry weight of beta glucan, a non-digestible polysaccharide. The wet algae meal is transferred to mixer (3), such as a mixing tank or any piece of equipment capable of mixing (e.g., ribbon blender). Optionally, the pH of the polysaccharide solution can be adjusted by the addition of acid or base (A).

A concentrated solution of a soluble metal salt (B), such as $ZnSO_4$-$H_2O$, can be added to the mixer (3) and mixed vigorously with the polysaccharide solution for 1-120 minutes. Any water soluble metal salt (B) may be used, For example, the metal salt (B) can be mixed with the beta glucan so that the final product can be a copper polysaccharide complex, zinc polysaccharide complex, iron polysaccharide complex, cobalt polysaccharide complex, magnesium polysaccharide complex, manganese polysaccharide complex, and combinations thereof. Preparation of the soluble metal salt (B) solution may involve heating a mixture of the metal salt (B) in water with mixing. Optionally, this mixer (3) may be heated or cooled. Optionally, the mixer (3) may be heated to the temperature required to pasteurize the material and inactivate enzyme activity. When the polysaccharide solution and metal salt (B) solution are mixing, some amount of complexation will occur between the metal ions and the polysaccharides present in the wet algae meal such that the final product may be considered a metal polysaccharide complex.

After the desired amount of mixing, the mixture is transferred to a dehydrator (4), which is any device capable of drying the material. For example, the dehydrator (4) may be a tray dryer, belt dryer, rotary drum dryer, etc. Once the material contains less than 10% moisture, it is transferred to a mill (5) where its patlicle size is reduced to less than 500 µm. More preferably, its pailicle size is reduced to less than 250 µm. Once the material has been milled, it is packaged (6) into containers of suitable size and labeled. Optionally, the addition of the metal salt (B) solution to the wet algae meal may be omitted and the resultant product will be algae meal.

With reference to FIG. 6, another embodiment of a fermentation process is shown. Algae biomass is produced in a fermenter (7) under sterile conditions on chemically defined media. Optionally, algal biomass may be produced in a growth tank under non-sterile conditions using any media that contains only feed-grade materials and is free of harmful substances (e.g., heavy metals, toxins, dangerous chemicals). After the desired amount of time in the fermenter or growth tank (7), the fermenter broth is transferred to a mixer (8), such as a mixing tank or any piece of equipment capable of providing mixing (e.g., ribbon blender). The fermenter broth contains a mixture of whole algae cells, algae cell fragments, and polysaccharides granules. In the case of a non-sterile growth tank, low levels of non-algal biomass may also be present. Optionally, the pH of the fermenter broth is adjusted by addition of acid or base chemicals (C) to the mixer (8) to lyse cells, thereby releasing the majority of the polysaccharide granules from within the cells. This may be accomplished by adding base (e.g., NaOH) to the fermenter broth. Optionally, the broth may also be processed mechanically through a high-pressure homogenizer or ultrasonic cell disruptor to lyse cells. Optionally, the broth may be adjusted to an alkaline pH and then neutralized prior to centrifugation. After sufficient time that most if not all cells are lysed, the resultant mixture is transferred to a centrifuge (9) that dewaters the broth to produce two process streams: a crude polysaccharide solution (D); and mixture of other biomass materials (E).

The crude polysaccharide solution (D) is transferred to a mixer (10), such as a mixing tank or any piece of equipment capable of providing mixing (e.g., ribbon blender). The crude polysaccharide solution may optionally be washed with water or a suitable alcohol (ethanol, isopropanol) to remove non-polysaccharide materials. Additional washes may be performed with any chemical suitable to remove non-polysaccharide materials. The pH of the crude polysaccharide solution (D) may optionally be adjusted with acid or base (F).

A concentrated solution of a soluble metal salt (G), such as ZnSO4-H2O, is prepared and added to the mixing tank (10) and mixed vigorously with the polysaccharide solution for 1-120 minutes. Any water-soluble metal salt may be used, such that the final product can be, for example, a copper polysaccharide complex, zinc polysaccharide complex, iron polysaccharide complex, cobalt polysaccharide complex, magnesium polysaccharide complex or manganese polysaccharide complex. Preparation of the soluble metal salt solution may involve heating a mixture of the metal salt in water with mixing. Optionally, mixer (10) may be heated or cooled. Optionally, the mixer (10) may be heated to the temperature required to pasteurize the material and inactivate enzyme activity. When the polysaccharide solution and metal salt solution are mixing, some amount of complexation will occur between the metal ions and the polysaccharides present such that the final product may be considered a metal polysaccharide complex.

After the desired amount of mixing, the mixture is transferred to a dehydrator (11), which is any device capable of drying the material. For example, the dehydrator (11) may be a tray dryer, belt dryer, rotary drum drier, etc. Once the material contains less than 10% moisture, it is transferred to a mill (12) where its particle size is reduced to less than 500 µm. More preferably, its particle size is reduced to less than 250 µm. One the material has been milled, it is packaged (13) into bags of suitable size and labeled.

The non-polysaccharide material (E) contains partially hydrolyzed proteins and amino acids and is transferred to a mixer (14), such as mixing tank or any piece of equipment capable of providing mixing (e.g., ribbon blender). The pH of the non-polysaccharide material (E) may optionally be adjusted with acid or base (H), A concentrated solution of a soluble metal salt (I), such as ZnSO4-H2O is prepared and added to the mixer (14) and mixed vigorously with the amino acid-rich material for 1-120 minutes. Any water-soluble metal salt may be used, such that the final product can be, for example, a copper proteinate, zinc proteinate, iron proteinate, cobalt proteinate, magnesium proteinate, manganese proteinate, and combinations thereof. Preparation of the soluble metal salt solution may involve heating a mixture of the metal salt in water with mixing. Optionally, mixer (14) may be heated or cooled. Optionally, the mixer (14) may be heated to the temperature required to pasteurize the material and inactivate enzyme activity. When the non-polysaccharide solution and metal salt solution are mixing, some amount of complexation will occur between the metal ions and the partially hydrolyzed proteins and amino acids present such that the final product may be considered a metal proteinate.

After the desired amount of mixing, the mixture is transferred to a dehydrator (15), which is any device capable of drying the material. For example, the dehydrator (15) may be a tray dryer, belt dryer, rotary drum drier, multi-effect evaporator, etc. Once the material contains less than 10% moisture, it is transferred to a mill (16) where its particle size is reduced to less than 500 µm. More preferably, its particle size is reduced to less than 250 µm. Once the material has been milled, it is packaged (17) into bags of suitable size and labeled. Optionally, the addition of the metal salt solution to each process stream (D, E) may be omitted and the resultant products will be a relatively pure polysaccharide and partially hydrolyzed protein meal.

Advantages to complexing the trace metal and the beta glucan include an increase in the bioavailability of the trace metal in combination with the immune system modulating aspects of beta glucan. The beta glucan is indigestible in the gut and can shield the trace metal from binding to an agonist until it is released in the intestine, for example. Furthermore, because some trace elements, such as zinc, are typically required in the diet in order to obtain optimal immune system functionality, the combination with an immune enhancing compound such as beta glucan can be more preferable in some situations for combining into an animal feed or vitamin premix blend than combining the same trace metal with another source, such as an amino acid or protein, which can also be provided as a separate product. The present processes demonstrate the capability of *Euglena*-derived beta glucan to bind or absorb large enough concentrations of zinc and other trace metals to deliver significant concentrations of the trace metal in an animal diet.

Some embodiments of a metal beta glucan complex include a member selected from the group consisting of a copper beta glucan complex, zinc beta glucan complex, iron beta glucan complex, cobalt beta glucan complex, magnesium beta glucan complex, molybdenum beta glucan complex, manganese beta glucan complex, and combinations thereof.

Although any trace-mineral containing inorganic salt may be used, some examples of salts include those that are commodities already used commercially as feed ingredients. Examples of such inorganic salts include but are not limited to metal sulfates, metal oxides, metal chlorides, hydrated metal salts, metal acetates, metal bromides, metal iodides, metal phosphates, metal selenites, and combinations thereof, where a pot lion of the salt can include iron, magnesium, lithium, zinc, copper, chromium, nickel, cobalt, vanadium, molybdenum, manganese, selenium, tungsten, iodine, and combinations thereof.

In some embodiments, the resulting metal polysaccharide complex includes 3% to 25% by weight metal and at least 25% by weight beta glucan. In certain cases, the polysaccharide portion of the product can be comprised of at least 50% by weight beta glucan. Zinc sulfate or zinc oxide may be used as the trace mineral-containing salt to make a zinc beta glucan complex, where the zinc beta glucan complex can comprise at least 1% by weight zinc on a dry weight basis that can be administered at less than 3% by weight total inclusion in an animal's diet.

Measuring the Effects of Beta Glucan

The animal feed composition described herein is expected to generally modulate the immune system. Ultimately, such benefits can translate into improved general well-being and health in animals, and improved economics of livestock production, especially in livestock production methods that do not employ a sub-therapeutic use of antibiotics in the water or in animal feed. Methods to evaluate use of the present compositions in animal teed include measuring increases in antibody titers, measuring increases in the activity of immune system cells (e.g., rates of phagocytosis and natural killer cell cytotoxicity), measuring improvements in feed conversion efficiency, measuring decreased stress, measuring improved weight loss or weight gain, measuring improvements in feed consumption, measuring improvements in average daily gain, performing challenge studies where at least one of the treatment groups is administered a composition as described herein, measuring reduced mortality rates in an animal population, measuring alternations in levels of interleukins or other cytokines which are known to be related to immunological performance, measuring effects on tumor necrosis factor alpha, fluorescently tagging components of the compositions described herein and observing their presence or metabolism in various cell, blood, or tissue samples, performing general histological analysis on animals that are fed a composition described herein, weighing the organs or animals which are fed a composition described herein, or any other analysis that demonstrates a significant effect on animals when they are fed one or more of the compositions described herein.

Animal Feed Milk Replacer

The present animal feed compositions can be formulated as a milk replacer, where a milk replacer is a product that is fed to a young mammal as a supplement, or a replacement for the mother's natural milk. Milk replacer products exist for a wide range of mammals, including but not limited to cows, goats, lambs, sheep, squirrels, humans, and even exotic zoo animals. Some mammals, such as cows, have a ruminant digestive system. However, young ruminants do not have fully developed or functional digestive systems-organs that produce digestive enzymes are not fully functional at birth. These young ruminants suffer from variations in diet, and are particularly vulnerable to infection and stress. Milk replacer comprising crude protein, crude fat, whey, and other substances is often provided to young cows in order to reduce variability in their diet and also because it can be more economic to feed them milk replacer and to sell the mother's milk.

Milk replacers usually contain some combination of components of the following substances: whey protein, fat, crude protein, emulsifier, flow agent, dicalcium phosphate, lysine, vitamins, trace minerals, calcium carbonate, choline, flavor compounds, ash, calcium and phosphate. Sources of fats and proteins can be animal or plant-based. Different fat compositions, as measured by hydrocarbon chain length, and protein composition, as measured by amino acid components, have been shown to yield different outcomes in terms of feed conversion efficiency, weight gain, growth rates, mortality, and overall resistance to infections.

The present technology includes an animal feed composition that is formulated as a milk replacer, where the milk replacer can include protein, fat, and beta glucan in order to provide substantive calories and to enhance the well-being of a mammal. Also included is a method of stimulating an increase in body weight and for enhancing the well-being of a young mammal by feeding it a milk replacer product comprising of protein, fat and beta glucan.

EXAMPLES

Beta Glucan Branching Analysis

A branching analysis was performed on beta glucan extracted from *Euglena gracilis* grown using a heterotrophic, sterile fermentation approach.

The following methods were employed.

Cell culture and beta glucan measurements. Two cultures of *Euglena* were each grown on a media containing major and minor essential nutrients (including nitrogen, phosphorus), trace minerals, and vitamins (B1 and B12) as is common for the growth of this species. The 200 ml cultures were bubbled with air in 250 ml Erlenmeyer flasks to provide oxygen, carbon dioxide, and mixing of the cultures. Initial *Euglena* density was 0.7 g L"1·Both cultures were exposed to light levels of 150 μmol photon m s·1 and 4 g L"1 of fixed carbon was dosed as a supplemental carbon treatment to one culture. After two days, the samples were measured for total suspended solids to determine the dry weight of the biomass. Beta glucan content was determined by lysing the cells and centriffiging the beta glucan crystals. Approximately 1 part *Euglena* biomass (dry weight basis) is suspended in 5 pails water and 10 patis of (10 g/L sodium dodecyl sulfate). This solution mixed vigorously and then heated to 100 deg C. for 30 minutes. The solution is then cooled and centrifuged at >500 g for 5 minutes. The supernatant is discarded and the pellet is washed by re-suspension in 10 patis water, mixed vigorously and centrifuged at >500 g for 5 minutes. The washing process is repeated 2 more times with 10 patis of 70-95% ethanol, to arrive at a purified beta glucan pellet. The pellet can further be dried to a white/tan powder under a vacuum at 65 deg C. FIG. 7 shows the mass in dry weight per liter of *Euglena* and beta glucan grown in the control media and a media having the supplement carbon treatment. FIG. 8 shows the percent beta glucan by dry weight of *Euglena* grown in control media and the media having the supplemental carbon treatment.

Per-O-methylation and linkage analysis. For glycosyl linkage analysis, two samples of beta glucan extracted using the methods above, were permethylated, depolymerized, reduced, and acetylated; the resulting partially methylated alditol acetates (PMAAs) were analyzed by gas chromatography-mass spectrometry (GC-MS) as described by York et al (1985) Methods Enzymol. 118:3-40.

Initially, dry sample was suspended in about 300 µl of dimethyl sulfoxide and placed on a magnetic stirrer for 1-2 weeks. The sample was then permethylated by the method of Ciukanu and Kerek (1984) Carbohydr. Res. 131:209-217 (treatment with sodium hydroxide and methyl iodide in dry DMSO). The sample was subjected to the NaOH base for 10 minutes then methyl iodide was added and left for 40 minutes. The base was then added for 10 minutes and finally more methyl iodide was added for 40 minutes. This addition of more methyl iodide and NaOH base was to insure complete methylation of the polymer. Following sample workup, the permethylated material was hydrolyzed using 2 M trifluoroacetic acid (2 h in sealed tube at 121° C.), reduced with NaBD4, and acetylated using acetic anhydride/trifluoroacetic acid. The resulting PMAAs were analyzed on a Hewlett Packard 5975C GC interfaced to a 7890A MSD (mass selective detector, electron impact ionization mode); separation was performed on a 30 m Supelco 2330 bonded phase fused silica capillary column,

TABLE 5

Result of Per-O-Methylation and Linkage Analysis from 2 Extracted Beta Glucan Samples.

| Sample | β-glucan 1 | β-glucan 2 |
|---|---|---|
| glycosyl residue | PKaren % | |
| terminally-linked glucopyranosyl residue (t-glc) | 0.34 | 0.3 |
| 3-linked glucopyranosyl residue (3-glc) | 93.03 | 94.1 |
| 4-linked glucopyranosyl residue (4-glc) | 2.25 | 2.4 |
| 2,3-linked glucopyranosyl residue (2,3-glc) | 3.47 | 2.3 |
| 3,6-linked glucopyranosyl residue (3,6-glc) | 0.36 | 0.8 |
| 2,3,4-linked glucopyranosyl residue (2,3,4-glc) | 0.55 | 0.1 |
| Total | 100.0 | 100.0 |

Linkage results indicate that both samples are mainly composed of 3-linked glucopyranosyl residues. Minor amounts of 4- and 2,3-linked Glc residues are detected along with negligible amount of 3,6-linked, terminal and 2,3,4-linked Ole.

Immune Response Parameters in Mice

A study was conducted in collaboration with Dr. Vaclav Vetvicka in the Department of Pathology at the University of Louisville in order to determine if paramylon was an effective immune stimulant in mammals when provided as a feed ingredient. Objectives included:
1. Determining whether paramylon stimulated the immune system of mice when dosed orally;
2. Comparing the effects of paramylon vs. other beta glucan products used in animal feed supplements at various dosage levels; and
3. Evaluating the effectiveness of whole cell paramylon vs. extracted and purified paramylon, The following methods were employed.

Algal biomass containing beta glucan was grown using fermentation processes as described herein. Two different whole cell products (WBG50A and WBG50B) and one purified beta glucan extract were tested in this mouse study. The WBG50A sample was produced from cells grown on glucose as the organic carbon source, whereas the WBG50B sample was produced from cells grown on ethanol. Both whole cell products contained about 50 wt. % beta-1,3 glucan and were centrifuged and then dried without any further processing. Fractionating the WBG50A biomass to isolate the beta glucan and then repeatedly washing the beta glucan fraction to remove non-beta glucan cell components produced the "extract" sample. The extract contained about 93 wt. % beta-1,3 glucan.

The whole cell biomass samples, beta glucan extract, and other beta glucan products were all dried and ground to particle sizes of less than 500 microns. These dry powders were then mixed with PBS buffer and diluted to appropriate concentrations before being dosed by gavage to the mice. Three BALB/c mice were allocated to each treatment group and given varying levels of beta glucan on a weight percent of their total diet basis, ranging from less than 0.001% to 0.25% of the mouse diet ration on day I of the experiment. Only the data from the 0.005% and 0.05% dosing levels are represented here.

Blood was taken from each mouse to measure non-specific immune system activity. The following parameters were assessed: phagocytosis activity (the ability of macrophages to ingest foreign pa11ides), natural killer (NK) cell activity (the ability of NK cells to destroy foreign or infected cells), and cytokine concentrations (IL-2). To measure the capacity of the specific immune response, antibody formation in response to ovalbumin was measured via enzyme-linked immunosorbent assay (ELISA) using a Freund adjuvant as a positive control and PBS as the negative control.

The following results were obtained.

Phagocytosis is one response by the immune system to capture and destroy potentially harmful particles (e.g., bacteria). The phagocytosis index was measured as the percent of neutrophils that actively captured and engulfed labeled particles. Mice that were given only the PBS control had a phagocytosis index of30% (see FIG. 9). The highest recorded index (45%) was observed for mice fed the 0.05% dose of WBGS0B, which is a 50% increase over the control treatment. Overall, the WBG50B treatment had the highest phagocytosis index of all the treatments at each of the two dosage levels, and was especially effective compared to all of the treatments at the lowest dosage level (0.005% of diet).

NK Cell Activity is an index of the ability for isolated natural killer (NK) cells from the spleen to kill target cells (e.g., YAC-1 cells from a T-lymphoma cell line) during a 4-hour incubation. Mice that were fed the PBS control displayed a cytotoxicity index of 12%, while the mice fed the 0.05% dose of WBGS0B had a cytotoxicity index over three times higher (38.5%, see FIG. 10). Both the WBGS0B and the extract treatments substantially outperformed other beta glucan products (Fibosel, Biomatrix) at both dosage levels, and in some cases, the WBGS0B treatment showed nearly twice the NK cell activity response, as reflected by cytotoxicity, of Fibosel at the 0.05% and 0.005% dosage levels.

Interleukin-2 (IL-2) is an imp011ant cytokine-messaging molecule that helps regulate the immune response to microbial infection. IL-2 production is measured as the amount of IL-2 produced by harvested spleen cells during an incubation period. IL-2 response is a more generalized immune response than NK cell activity, phagocytosis, and antibody formation. As such, many different types of foreign compounds, not just beta glucan, can elicit an increase in IL-2 production. Mice that were fed the PBS control did not observe an increase in IL-2 production, while all of the beta glucan product treatments elicited a very strong IL-2 response that was noticeably increased at the higher dosage rate (see FIG. 11). The extract treatment resulted in the highest IL-2 production, followed by the other beta glucan products (Fibosel, Biomatrix), and then the WBG50 products.

Antibody formation indicates that beta glucan can act as an adjuvant (enhancer) for vaccines. Mice were injected with ovalbumin (egg white protein, a model antigen) on day 0 and day 14 while being fed each beta glucan product daily for 21 days. On day 21, the number of antibodies to ovalbumin are measured in the serum. Freund adjuvant (an emulsion of inactivated bacteria cells) was used as a positive control as it is recognized as an industry standard for inducing antibody formation. However, Freund adjuvant is not used in many animals including humans because of its strong toxicity effect. As expected, the Freund adjuvant produced a very high level of antibodies (see FIG. 12). At the 0.05% dosage rate, both whole cell samples and the competing products each elicited similar antibody production at about 20% the level of the Freund adjuvant. The extract sample produced a much stronger antibody response for the 0.05% dosage rate, reaching nearly 55% of the level induced by the Freund adjuvant.

These experiments establish the following precepts with respect to the present technology:
1. Each of the *Euglena* beta glucan containing products (WBG50A, WBG50B, Extract) induced significant increases in each of the immune responses measured (phagocytosis, NK cell activity, IL-2 production, antibody production) compared to controls.
2. For each measure of immune response, the *Euglena* beta glucan products performed as well, and in many cases, better than the other beta glucan products Fibosel and Biomatrix. In particular, WBG50B (whole cell biomass grown on ethanol as the carbon source), demonstrated the highest measured levels for phagocytosis and NK cell activity.
3. The extracted *Euglena* beta glucan product elicited a very strong antibody response that exceeded 50% of the level induced by a Freund adjuvant, indicating the potential for adjuvant applications.
4. With the exception of antibody production, the immune response to whole cell biomass was as high, if not higher, than the extracted *Euglena* beta glucan alone. This suggests that other components of the algae cells (e.g., omega-3 fatty acids, vitamin E, trace metals) can have a synergistic effect with the beta glucan to induce a stronger immune response.
5. In all cases, the immune response to the dosage levels (0.005% and 0.05%) was not linear (i.e., 10× higher) and differed among products, suggesting that the optimal dosage rate for the *Euglena* beta glucan products is likely much lower than the highest dosage level (0.05%). Notably, the immune response in NK cell activity and phagocytosis for the lowest dosage of WBG50B was even higher than the for highest dosage level for Fibosel and Biomatrix, suggesting the possibility for reduced dosing requirements for *Euglena* beta glucan. Additionally, dosage rates can be optimized for the phagocytosis response which is the first line of defense against pathogens.

Efficient Production of Beta Glucan using Heterotrophic Fermentation of *Euglena gracilis*

In order to determine optimal production of beta glucan with other synergistic co-products using *Euglena gracilis*, a wide range different growth media formulations, pH, temperature controls, light conditions, and genetic strains of *Euglena* were tested. Unexpectedly, it was determined that *Euglena gracilis* produced greater quantities of valuable proteins and antioxidant lipids when grown in photosynthetic conditions. However, *Euglena* that was grown heterotrophically in dark, sterile fermentation vessels produced greater quantities of beta-1,3-glucan. Mice that were fed dried *Euglena gracilis* derived from sterile fermentation vessels showed immune system performance that exceeded beta glucans derived from yeast sources, or from *Euglena* that contained smaller quantities of beta glucans.

Unlike other reports that describe production of vitamin E and other antioxidants using algae grown photosynthetically, *Euglena gracilis* grown heterotrophically appears to produce beta glucan that is better suited for animal feed applications.

Furthermore, the present experiments determined that it is important to quickly dry the algae as part of the manufacturing process in order to prevent the breakdown of valuable carotenoids and other antioxidants. It should be noted that in some cases it can be economically beneficial to store a wet algae slurry for an extended period of time before drying. In one embodiment, freshly centrifuged algae can be preserved by heating the material in glass jars or retort pouches, similar to how food stuffs are canned for long term storage at room temperature. This information was used in developing the manufacturing processes described herein and illustrated in FIGS. 5 and 6.

TABLE 6

Examples of Compound Concentrations in *Euglena* Samples (dry weight basis)

| | Concentration in wet sample stored at room temperature for 2 days | Concentration in sample dried immediately after centrifuging |
| --- | --- | --- |
| Lutein | 80 ppm | 145.7 ppm |
| Zeaxnthin | 17.2 ppm | 2.9 ppm |
| Astaxanthin | 7.4 ppm | 7.6 ppm |
| Beta-carotene | 9.4 ppm | 59.3 ppm |
| DHA | No data | 0.33% |
| EPA | No data | 0.33% |
| Alpha tocopherol | 126 IU/kg | 34 IU/kg |

*E. coli* Challenge in Mice

Objectives of this example include:
1. Determining whether oral doses of *Euglena* algae meal and purified beta glucan products increase survival against a lethal dose of the bacterium *Escherichia coli* (*E. coli*);
2. Determining whether *Euglena* algae meal and beta glucan products specifically stimulated the immune system of mice as measured by antibody production, NK killer cell cytotoxicity, and phagocytosis activity; and
3. Comparing the effects of *Euglena* algae meal and purified beta glucan products to a other beta glucan products derived from yeast at varying dosage levels.

The following methods were employed.

*Euglena* cells were grown in a sterile fermenter. Once the target density of biomass was reached in the fermenter the cells were centrifuged and the resulting paste was stored frozen at −20° C. To produce the algae meal sample, the frozen paste was thawed, dried at 65° C. until it formed a dry flake, and then ground to a particle size of less than 250 microns. The purified algae beta glucan sample was produced by fractionating the *Euglena* cells and isolating the beta glucan through a proprietary purification process that results in an extract with >90% beta glucan and a particle size of less than 250 microns. An extracted, yeast-derived beta glucan product, Macrogard, which guarantees >60% beta glucan, was procured from a commercial distributer and used "as-is" without further modifications. Each dry product was mixed with phosphate buffered saline (PBS) and diluted to appropriate concentrations before being dosed by gavage to the mice at prescribed dosing levels.

All animal work was conducted in the laboratory of Dr. Vaclav Vetvicka in the Department of Pathology at the University of Louisville. Dr. Vetvicka is well known for his research on the physiological effects of beta glucan and his lab has conducted numerous side-by-side comparisons of beta glucan products to determine their potential effectiveness.

E. coli Bacteria. Challenge, Ten BALB/c mice were allocated to each treatment group and received a nominal lethal dose of E. coli (3×107) via intramuscular injection on day 0. Beta glucan products (0.01% of the daily feed ration by weight) were orally dosed by gavage to the mice daily starting two days prior to the injection (day −2) through two days following the injection (day +2). The control group received only a PBS gavage, while an antibiotic-treated group received oral doses of Ampicillin (13 mg/kg) on days 0, 1, 2, 3 and 4, Mice were evaluated daily up through day 10.

Antibody Titers. Three BALB/c mice were allocated to each treatment group and received daily oral dose of beta glucan products equivalent to 0.002, 0.005, 0.010 and 0.020% of their daily feed ration by weight starting on day 0. The antigen (ovalbumin) was given by intraperitoneal injection on days 3 and 16 and antibody titer production was measured on day 23 using an ELISA assay with a Freund adjuvant as a positive control and PBS as the negative control.

NK Cell Cytotoxicity and Phagocytosis Activity. Nine BALB/c mice were allocated to each treatment group and fed beta glucan products in the same manner as the antibody titer experiment explained above in order to measure natural killer (NK) cell cytotoxicity (the ability of NK cells to destroy foreign or infected cells) and phagocytosis activity (the ability of macrophages to ingest foreign particles), On days 1, 7, and 14, three mice from each treatment group were sacrificed to harvest material for analyses. NK cell activity (measured as cytotoxicity) is an index of the ability for isolated NK cells from the spleen to kill target cells (e.g., YAC-1 cells from a T-lymphoma cell line) during a 4 hour incubation. The phagocytosis index is measured as the percent of neutrophil cells that actively capture and engulf labeled particles in an allotted time.

These experiments produced the following results.

E. coli Bacteria Challenge (see FIG. 13). All mice in the control group, which received only PBS, died within seven days of the E. coli injection. In contrast, mortality at day 10 was decreased in all treatment groups by at least 40%. Notably, 70% of the mice receiving the purified algae beta glucan product survived 10 days following E. coli injection. This treatment group and the one receiving Ampicillin showed very similar survival rates over time, suggesting that the Euglena-derived beta glucan treatment promoted similar antibacterial activity to Ampicillin. Mice receiving algae meal, which contains about 50% beta glucan, also showed a significant decline in mortality compared to the control group. In this treatment group, 50% of the mice survived 10 days following E. coli injection compared to 40% surviving in the group fed a yeast-derived beta glucan extract product (Macrogard).

Antibody Titers (see FIG. 14). A significant increase in antibody titer indicates the potential for a product like beta glucan to serve as an adjuvant (enhancer) to vaccines. As expected, the positive control (Freund adjuvant, an emulsion of inactivated bacteria cells) produced very high levels of antibodies to ovalbumin, However, Freund adjuvant is toxic and is not actually used in animals or humans as an adjuvant. All of the beta glucan treatment groups elicited an increase in antibody production that also increased with dosage rate. The purified algae beta glucan treatment produced the most antibodies at each of the treatment dosage levels followed closely by the algae meal treatment group. The Macrogard yeast beta glucan extract treatment group demonstrated substantially lower (between 15% and 50% lower) antibody titers than the purified algae beta glucan and algae meal treatments at moderate dosing levels (0.005 and 0.010%) but matched the algae meal treatment at the highest dosage rate.

NK Cell Cytotoxicity (see FIG. 15). NK cell cytoxicity is an index of the non-specific immune response by NK cells to kill potentially pathogenic organisms. Mice that were fed the PBS control displayed a cytotoxicity index of 12%, while the mice fed with doses as low as 0.005% of either the algae meal or purified algae beta glucan demonstrated a cytotoxicity index over three times higher (36% to 50%). At doses of 0.005% and higher, both the algae meal and purified algae beta glucan treatments elicited a stronger cytotoxicity response than the Macrogard yeast beta glucan extract treatments.

Phagocytosis Activity (see FIG. 16). Phagocytosis is another non-specific immune response to engulf potentially pathogenic organisms. Mice that were given only the PBS control had a phagocytosis index of 30% while mice fed the highest dose of the purified algae beta glucan demonstrated nearly twice the phagocytosis activity (59%). As seen with the NK cell cytotoxicity and antibody titers, the purified algae beta glucan treatment group demonstrated the best performance at each dosage level. The algae meal and. Macrogard yeast beta glucan extract treatment groups demonstrated similar phagocytosis activity at the two lowest dosage levels, but mice fed Macrogard yeast beta glucan extract at the two highest dosage levels had slightly higher phagocytosis activity.

Accordingly, the data from these experiments demonstrate the following:

1. Each of the beta glucan products (algae meal, purified algae beta glucan, and Macrogard yeast beta glucan extract) increased the survivorship of mice exposed to a lethal dose of E. coli. In particular, the algae meal treatment increased survivorship at day 10 from 0% in the control group up to 50%. The purified algae beta glucan treatment increased survivorship up to 70%, which was the same response as the antibiotic treatment (Ampicillin). These data indicate that Euglena-derived beta glucan stimulates the immune system to provide potent antibacterial activity and that beta glucan within the algae meal, which has not been extracted and pwified, is readily bioavailable.
2. Both specific immune responses (i.e., antibody production) and non-specific immune responses (i.e., NK cell cytotoxicity and phagocytosis activity) increased significantly for treatment groups fed any of the beta glucan products. For all of the immune metrics, the purified algae beta glucan treatment group elicited the strongest immune response at all treatment levels.
3. Both algae meal and purified algae beta glucan products elicited a very strong antibody response that exceeded 50% of the level induced by a Freund adjuvant, indicating the utility of these products to serve as adjuvants.
4. Algae meal product performed as well, if not better, than the Macrogard yeast beta glucan extract product at nearly all treatment levels in both antibody production and NK cell cytotoxicity assays. In most cases, the algae meal product induced nearly the same or better response compared to Macrogard at only one-quarter to one-half the dosage level.

5. Macrogard yeast beta glucan extract elicited a lower phagocytosis response than the purified algae beta glucan product, but performed as well or better than the algae meal product. In general, the overall impact of all beta glucan products on phagocytosis is more tempered than the effects on NK cell cytotoxicity and antibody production.

6. These results corroborate earlier, shorter-duration (3 days) studies that found algae meal and purified algae beta glucan products to induce the enhanced immune responses compared to controls and other yeast beta glucan products, such as Fibosel yeast beta glucan extract and another generic yeast beta glucan product.

Example embodiments are provided so that this disclosure will be thorough, and will fully convey the scope to those who are skilled in the art. Numerous specific details are set f01th such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results

What is claimed is:

1. A method of stimulating an immune response in an animal, the method comprising feeding to the animal a composition comprising (i) heterotrophically grown Euglena comprising greater than 20 weight % beta-(1,3)-glucan, wherein the Euglena is grown and fermented in a fermenter under sterile conditions and dried to contain less than 10% moisture, and (ii) an animal feed component, wherein the beta-(1,3)-glucan is present in an amount from 0.001% to 0.020% of the total weight of the animal feed.

2. The method of claim 1, wherein the beta glucan consists essentially of unbranched beta-(1,3)-glucan.

3. The method of claim 1, wherein the beta glucan comprises greater than about 90% unbranched beta-(1,3)-glucan.

4. The method of claim 1, wherein the beta glucan comprises paramylon.

5. The method of claim 1, wherein the administering comprises adding the composition to the animal's diet.

6. The method of claim 1, wherein the animal feed component comprises a member selected from the group consisting of astaxanthin, lutein, beta-carotene, eicosapentaenoic acid, docosahexaenoic acid, omega 3 fatty acid, omega 6 fatty acid, alpha tocopherol, and combinations thereof.

7. The method of claim 1, wherein the beta-(1,3)-glucan is separated from other Euglena components.

8. The method of claim 1, wherein the average particle size of the Euglena is reduced to less than 500 µm.

9. A method of stimulating an immune response in an animal, the method comprising feeding to the animal a composition comprising (i) heterotrophically grown Euglena comprising greater than 20 weight % beta-(1,3)-glucan, wherein the Euglena is grown and fermented in a fermenter under sterile conditions and dried to contain less than 10% moisture, and (ii) an animal feed component, wherein the beta-(1,3)-glucan is at about 10 ppm to about 200 ppm in the animal feed, said beta glucan comprising greater than about 90% unbranched beta-(1,3)-glucan.

10. The method of claim 9, wherein the beta glucan consists essentially of unbranched beta-(1,3)-glucan.

11. The method of claim 9, wherein the beta glucan comprises paramylon.

12. The method of claim 9, wherein the administering comprises adding the composition to the animal's diet.

13. The method of claim 9, wherein the animal feed component comprises a member selected from the group consisting of astaxanthin, lutein, beta-carotene, eicosapentaenoic acid, docosahexaenoic acid, omega 3 fatty acid, omega 6 fatty acid, alpha tocopherol, and combinations thereof.

14. The method of claim 9, wherein the composition comprises an additional immune modulating, stress reducing, or other stimulant ingredient selected from the group consisting of alpha tocopherol, cholecalciferol, zinc, chromium, selenium, arginine, ascorbic acid, alklyglcerol, caffeine, kava kava, curcuma longa, spirulina, calcium D-glucarate, coenzyme Q10, peptides, dimethglycine, docosahexaenoic acid, ecosapentaenoic acid, alpha-lineolenic acid, astaxanthin, beta carotene, lutein, lactobacillus probiotics, bifidobacterium probiotics, mannoliggosaccharide, fructooliggosacharides, Astragalus, Echinacea, Esberitox, garlic, glutathione, kelp, L-arginine, L-ornithine, lecithin granules, extracts from maiitake, reishi or shiitake mushrooms, manganese, quercetin, bromelain, Olive Leaf, Sambucus, Umcka, panthothenic acid, quercetin, alpha lipoic acid, essential oils, fish oils, spices and their derivatives, pterostilbene, and combinations thereof.

15. The method of claim 9, wherein the beta-(1,3)-glucan is separated from other Euglena components.

16. The method of claim 9, wherein the average particle size of the Euglena is reduced to less than 500 µm.

* * * * *